US011541151B2

(12) United States Patent
Kim et al.

(10) Patent No.: US 11,541,151 B2
(45) Date of Patent: Jan. 3, 2023

(54) COACERVATE COMPOSITION CONTAINING PROTEIN DRUG AND WOUND HEALING AGENT COMPRISING SAME

(71) Applicant: CHA UNIVERSITY INDUSTRY-ACADEMIC COOPERATION FOUNDATION, Pocheon-si (KR)

(72) Inventors: Aeri Kim, Seongnam-si (KR); Seong Hee Jeong, Incheon (KR)

(73) Assignee: Cha University Industry-Academic Cooperation Foundation, Pocheon-si (KR)

( * ) Notice: Subject to any disclaimer, the term of this patent is extended or adjusted under 35 U.S.C. 154(b) by 0 days.

(21) Appl. No.: 16/824,222

(22) Filed: Mar. 19, 2020

(65) Prior Publication Data

US 2020/0215232 A1    Jul. 9, 2020

Related U.S. Application Data

(63) Continuation of application No. PCT/KR2018/011042, filed on Sep. 19, 2018.

(30) Foreign Application Priority Data

Sep. 20, 2017    (KR) .................. 10-2017-0121206

(51) Int. Cl.
*A61L 27/54*    (2006.01)
*A61L 27/22*    (2006.01)
*A61L 26/00*    (2006.01)

(52) U.S. Cl.
CPC ........... *A61L 27/54* (2013.01); *A61L 26/0052* (2013.01); *A61L 27/222* (2013.01)

(58) Field of Classification Search
CPC .............................. A61L 27/222; A61L 27/54
See application file for complete search history.

(56) References Cited

U.S. PATENT DOCUMENTS

| 5,023,024 | A | 6/1991 | Kyogoku et al. | |
|---|---|---|---|---|
| 6,916,490 | B1 * | 7/2005 | Garver ................. | A61K 9/1652 424/489 |
| 6,969,530 | B1 * | 11/2005 | Curtis .................. | A61K 9/5057 264/4.1 |
| 2014/0287061 | A1 | 9/2014 | Landolina | |
| 2015/0190372 | A1 | 7/2015 | Djedour | |
| 2016/0250375 | A1 | 9/2016 | Stewart | |

FOREIGN PATENT DOCUMENTS

| JP | S63-258641 A | 10/1988 |
|---|---|---|
| KR | 10-2010-0133117 A | 12/2010 |
| KR | 10-2014-0090670 A | 7/2014 |
| KR | 10-2015-0014522 A | 2/2015 |
| KR | 10-2016-0129459 A | 11/2016 |
| WO | WO 2016/025911 A1 | 2/2016 |

OTHER PUBLICATIONS

M. Saravanan, K. Panduranga Rao. "Pectin-gelatin and alginate-gelatin complex coacervation for controlled drug delivery: Influence of anionic polysaccharides and drugs being encapsulated on physicochemical properties of microcapsules," Carbohydrate Polymers 80 (2010) 808-816. (Year: 2010).*
Coacervate wound care—Google Scholar Search—Dec. 28, 2020 (Year: 2020).*
Ujwala A. Shinde and Mangal S. Nagarsenker. Characterization of gelatin-alginate complex coacervation ind j pharm sci May 2009. (Year: 2009).*
Q. Xu, et al. Preparation of Monodisperse Biodegradable Polymers. Small. Jul. 2009 ; 5(13): 1575-1581. (Year: 2009).*
N. R. Johnson, Trisha Ambe, Y. Wang. Lysine-based polycation, Acta Biomaterialia 10 (2014) 40-46 (Year: 2014).*
Google_scholar_Dec. 27, 2021_polydispersity_in_coacervation_alginate.pdf (Year: 2021).*
International Search Report dated Jan. 31, 2019 in International Application No. PCT/KR2018/011042, in 4 pages.
Coacervates : A Novel State of Soft Matter—An Overview J. Surface Sci. Technol., vol. 24, No. 3-4, pp. 105-124, 2008, H. B. Bohidar.
Heparin-Based Coacervate of FGF2 Improves Dermal Regeneration by Asserting a Synergistic Role with Cell Proliferation and Endogenous Facilitated VEGF for Cutaneous Wound Healing: Biomacromolecules, Just Accepted Manuscript Publication Date (Web): May 19, 2016 Jiang Wu, Jingjing Ye, Jingjing Zhu, Zecong Xiao, Chaochao He, Hongxue Shi, Yadong Wang, Cai Lin, Hongyu Zhang, Yingzheng Zhao, Xiaobing Fu, Hong Chen, Xiaokun Li, Lin Li, Jie Zheng, and Jian Xiao.
The Role of Growth Factors, Cytokines and Proteases in Wound Management Primary Intention: The Australian Journal of Wound Management vol. 9 Issue 4 (Nov. 2001) Traversa, B; Sussman, G.
Pharmaceutical perspectives of impaired wound healing in diabetic foot ulcer: Journal of Pharmaceutical Investigation (2016) 46:403-423, Hui-Chong Lau1, Aeri Kim.
Proteases and the Diabetic Foot Syndrome: Mechanisms and Therapeutic Implications: Diabetes Care, vol. 28, No. 2, Feb. 2005, Ralf Lobmann, MD Gregory Schultz, PHD Hendrik Lehnert, MD.
Devi et al., "Study of Complex Coacervation of Gelatin A with Sodium Carboxymethyl Cellulose: Microencapsulation of Neem (Azadirachta indica A. Juss.) Seed Oil (NSO)", International Journal of Polymeric Materials, vol. 60, No. 13—16 pages (2011).
Devi et al., "Preparation and Evaluation of Gelatin/Sodium Carboxymethyl Cellulose Polyelectrolyte Complex Microparticles for Controlled Delivery of Isoniazid", AAPS PharmSciTech, vol. 10, No. 4—8 pages (2009).

(Continued)

*Primary Examiner* — Michael P Cohen
(74) *Attorney, Agent, or Firm* — Knobbe, Martens, Olson & Bear, LLP

(57) ABSTRACT

The present disclosure provides a coacervate composition containing a protein drug, gelatin A, sodium alginate and an acid and a wound-healing agent including the same. The coacervate composition according to the present disclosure can be useful as a wound-healing material delivery system for effectively delivering a protein drug, particularly epidermal growth factor, to a wound site in the wound-healing field.

15 Claims, 14 Drawing Sheets

(56) References Cited

OTHER PUBLICATIONS

Devi et al., "Genipin crosslinked microcapsules of gelatin A and k-carrageenan polyelectrolyte complex for encapsulation of Neem (Azadirachta Indica A Juss.) seed oil", Polymer Bulletin, vol. 65, No. 4—16 pages (2010).

Devi et al., "Smart porous microparticles based on gelatin/sodium alginate polyelectrolyte complex", Journal of Food Engineering, vol. 117, No. 2—12 pages (2013).

* cited by examiner

Figure 1

| form | Clear | Coacervate | Coacervate |
|---|---|---|---|
| pH | 6.10 | 5.13 | 4.81 |
| Turbidity | 0.01 | 0.03 | 1.07 |

HWGA : SA (1:0.25)

| form | Clear | Coacervate | Coacervate |
|---|---|---|---|
| pH | 6.02 | 5.28 | 4.90 |
| Turbidity | 0.01 | 0.08 | 1.65 |

HWGA : SA (1:0.167)

| form | Clear | Coacervate | Aggregation |
|---|---|---|---|
| pH | 5.96 | 5.30 | 4.96 |
| Turbidity | 0.01 | 1.30 | — |

HWGA : SA (1:0.125)

| form | Clear | Aggregation | Aggregation |
|---|---|---|---|
| pH | 5.90 | 5.36 | 4.88 |
| Turbidity | 0.01 | — | — |

HWGA : SA (1:0.1)

Supernatant

M: marker
1: BSA as a control
2: 1:0.25 – 1.1mM acetic acid
3: 1:0.25 – 2.7mM acetic acid
4: 1:0.167 – 1.1mM acetic acid
5: 1:0.167 – 2.7mM acetic acid
6: 1:0.125 – 1.1mM acetic acid
7: 1:0.125 – 2.7mM acetic acid Pellet M: marker
1: BSA as a control
2: 1:0.25 – 1.1mM acetic acid
3: 1:0.25 – 2.7mM acetic acid
4: 1:0.167 – 1.1mM acetic acid
5: 1:0.167 – 2.7mM acetic acid
6: 1:0.125 – 1.1mM acetic acid
7: 1:0.125 – 2.7mM acetic acid M: marker
1: EGF as a control
2: GA:SA (1:0.25) 2.7 mM – Supernatant
3: GA:SA (1:0.25) 2.7 mM – Pellet
4: GA:SA (1:0.167) 2.7 mM – Supernatant
5: GA:SA (1:0.167) 2.7 mM – Pellet P: 100 ug/ml EGF
M: Marker
S: coacervate-supernatant
C: coacervate-Pellet

1h incubation

2h incubation

Incubation (37°C, 100rpm)
M: Marker
P: EGF as a control
P+T: 10 ug EGF+417 ug/ml Trypsin-EDTA
1:1-M+T: GA:SA 1:1 ratio Mixture+417 ug/ml Trypsin-EDTA
1:1-C+T: GA:SA 1:1 ratio Coacervate+417 ug/ml Trypsin-EDTA
1:0.4-M+T: GA:SA 1:0.4 ration Mixture+417 ug/ml Trypsin-EDTA
1:0.4-C+T: GA:SA 1:0.4 ratio Coacervate
 + 417 ug/ml Trypsin-EDTA 8 hours after wound

COACERVATE COMPOSITION CONTAINING PROTEIN DRUG AND WOUND HEALING AGENT COMPRISING SAME

CROSS-REFERENCE TO RELATED APPLICATIONS

This application is a continuation application, and claims the benefit under 35 U.S.C. § 120 and § 365 of PCT Application No. PCT/KR2018/011042, filed on Sep. 19, 2018, which is hereby incorporated by reference. PCT/KR2018/011042 also claimed priority to Korean Patent Application No. 10-2017-0121206 filed on Sep. 20, 2017 which is hereby incorporated by reference.

BACKGROUND

Technical Field

The present disclosure relates to a coacervate composition containing a protein drug and a wound-healing agent including the same, and more particularly to a coacervate composition containing a protein drug, gelatin A, sodium alginate and an acid and a wound-healing agent including the same.

Related Technology

A wound-healing process leads to tissue recovery and regeneration through complex cellular and biochemical steps (Traversa, B., Sussman G. *The Australian Journal of Wound Management* 2001; 9(4): 161-167). The physiological and cellular response to a wound proceeds in four stages in order to fully restore the anatomical and functional integrity of the injury site (Lobamann R, Schultz G., Lehnert H. *Diabetes care* 2005; 28(2):461-471). Specifically, the wound-healing stage is classically defined as homeostasis, inflammation (acute phase), proliferation (granulation and re-epithelialization) and reconstitution. These stages overlap each other somewhat, and are mostly regulated by cytokines and growth factors. Within 6 hrs. after tissue damage, platelets secrete cytokines, a variety of growth factors that attract inflammatory cells such as neutrophils, monocytes and granulocytes. They release reactive oxygen species (ROS) and proteases, which control bacterial contamination and clean wounds of cellular debris. The concentration of inflammatory cells reaches a maximum after 48 hrs., the end of the inflammatory phase, and the proliferation phases during the wound-healing process overlap to each other. Macrophages contribute to the wound-healing process until the proliferation stage. They secrete platelet-derived growth factor (PDGF), macrophage angiogenesis factor, and TGF-β two days after injury. PDGF, macrophage angiogenesis factor and angiotensin promote the formation of new blood vessels, creating granulation tissue specific to the wound. Epidermal growth factor (EGF), keratinocyte growth factor and PDGF stimulate epidermal cells to migrate and differentiate (keratinize), thus producing granulation tissue having a cell barrier resistant to drying and infection. Matrix metalloprotease (MMP) removes damaged extracellular matrix (ECM) protein, causing the cells to migrate, leading to angiogenesis and vasculogenesis in the wound.

However, chronic wounds such as diabetic ulcers do not progress to the above wound-healing process. Many studies have confirmed defects in wound healing that may be explained by the imbalance of dysfunctional cells and growth factors, proteases and cytokines (Lobamann R., Schultz G., Lehnert H. *Diabetes care* 2005; 28(2):461-471).

Unlike normal wound healing, the inflammatory response in intractable wounds, such as diabetic wounds, is prolonged and the protease response is correspondingly increased. In contrast to the balanced interaction of growth factor, cytokine, protease and extracellular matrix (ECM) during normal wound healing, in intractable wounds, the level of protease remains high at the wound site, leading to a decrease in wound healing due to degradation of matrix proteins and growth factors. Therefore, it is necessary to develop a growth factor delivery system for effective wound healing in intractable wounds such as those of diabetic foot ulcer (DFU).

Meanwhile, epidermal growth factor (EGF) plays an important role in wound healing. EGF is a polypeptide comprising 53 amino acids first isolated from the mouse submaxillary gland by Cohen. EGF stimulates the proliferation and migration of epidermal cells, fibroblasts and endothelial cells and promotes epidermal regeneration, angiogenesis and granulation tissue formation. The efficacy of EGF on wound healing has been reported experimentally and clinically for acute, chronic and burn wounds (Lau, H. C., Kim, A. *Journal of Pharmaceutical Investigation* 2016; 46(5):403-423). Many DFU medicaments using growth factors are commercially available. For example, Regranex includes recombinant human-platelet-derived growth factor (PDGF), and Fiblast is includes recombinant human basic fibroblast growth factor (bFGF). EGF is commercially available as Easyef (Daewoong Pharmaceutical, Seoul) in Korea, and is sold in China and some countries in South America. However, medicaments containing growth factors face several problems, such as limited wound closure and clinical efficacy, low stability during storage/distribution at room temperature, and safety issues due to systemic distribution after topical application. The limited efficacy is due to the large number of proteases present at the wound site because growth factors are degraded by the proteases immediately upon application to the wound site. Thus, one way to enhance the efficacy of EGF is to protect EGF from proteases by appropriate drug delivery systems. Accordingly, many delivery systems such as ointments, hydrogels, and nano/fine particles are being studied for the encapsulation and controlled release of EGF. However, problems of low loading efficiency and high denaturation rate in these systems have not yet been solved (Wu, J., et al., *Biomacromolecules* 2016; 17:2168-2177).

SUMMARY OF CERTAIN INVENTIVE ASPECTS

The present inventors have studied drug delivery systems capable of maximizing wound-healing efficiency by effectively encapsulating a protein drug so that the protein drug is effectively protected from protease at intractable wound sites in which the concentration of protease is high, and thus have ascertained that coacervate may be efficiently formed in a coacervate composition containing gelatin A, sodium alginate and an acid, which is a coacervate system in which anionic and cationic polymer electrolytes are controlled under appropriate conditions, whereby the protein drug may be effectively encapsulated. Moreover, the coacervate-lyophilized formulation may exhibit a wound closure effect and a sustained drug release effect, which may be expected to improve a wound-healing effect.

One inventive aspect is to provide a coacervate composition (especially a lyophilized formulation) containing a protein drug, gelatin A, sodium alginate and an acid, and a wound-healing agent including the same.

Another aspect provides a coacervate composition containing a protein drug, gelatin A, sodium alginate and an acid.

In an embodiment of the present disclosure, gelatin A may have an average molecular weight of 20 to 25 KDa, the ratio of gelatin A:sodium alginate may correspond to a weight ratio of 1:0.2 to 1.2, and the acid may be 5.4 to 16.3 mM acetic acid.

In another embodiment of the present disclosure, in the coacervate composition, the ratio of gelatin A:sodium alginate may correspond to a weight ratio of 1:1 and the acid may be 5.4 to 16.3 mM acetic acid, the ratio of gelatin A:sodium alginate may correspond to a weight ratio of 1:0.8 and the acid may be 5.4 to 10.9 mM acetic acid, or the ratio of gelatin A:sodium alginate may correspond to a weight ratio of 1:0.4 and the acid may be 5.4 to 8.2 mM acetic acid, and preferably, the ratio of gelatin A:sodium alginate is a weight ratio of 1:1 and the acid is 16.3 mM acetic acid, or the ratio of gelatin A:sodium alginate is a weight ratio of 1:0.4 and the acid is 8.2 mM acetic acid.

In another embodiment of the present disclosure, the protein drug may be at least one selected from the group consisting of epidermal growth factor (EGF), growth hormone (GH) and fibroblast growth factor (FGF).

Another aspect of the present disclosure provides a wound-healing agent including the coacervate composition.

In another embodiment of the present disclosure, the wound may be a chronic intractable wound, which may be a diabetic ulcer, particularly a diabetic foot ulcer.

In order to apply a coacervate system to wound healing, epidermal growth factor as a protein drug, sodium alginate as an anionic polymer, and gelatin A as a cationic polymer are used, and changes in physical properties such as turbidity, particle size, polydispersity index, zeta potential, etc. of coacervate depending on changes in pH, the ratio of sodium alginate and gelatin A, and the molecular weight of the polymer are measured, whereby the optimal coacervate composition can be determined based on turbidity and capture capacity of epidermal growth factor. Accordingly, the optimal epidermal growth factor-coacervate system of the present disclosure thus obtained is a coacervate composition containing a protein drug, gelatin A, sodium alginate and an acid, and a precipitate is formed in all ranges of coacervate conditions using high-molecular-weight gelatin, whereas the coacervate composition of the present disclosure using low-molecular-weight gelatin does not precipitate but forms coacervate under the same conditions as when using the high-molecular-weight gelatin, and exhibits high epidermal growth factor encapsulation efficiency. Moreover, in the proteolytic experiment using trypsin, epidermal growth factor can be effectively protected from protease, sustained release of epidermal growth factor from the coacervate system is confirmed, the cell proliferation and migration promotion effects are excellent, and the wound can be effectively sutured in a wound animal model.

Therefore, the coacervate composition containing a protein drug, gelatin A, sodium alginate and an acid according to the present disclosure can be useful as a wound-healing material delivery system for effectively delivering a protein drug, particularly epidermal growth factor, to a wound site in the wound-healing field.

BRIEF DESCRIPTION OF DRAWINGS

FIG. 1 shows the results of observation of polymer composite mixtures formed at various polymer ratios and acetic acid concentrations (0 mM, 1.1 mM, 2.7 mM);

DETAILED DESCRIPTION OF CERTAIN INVENTIVE EMBODIMENTS

Figure 2:
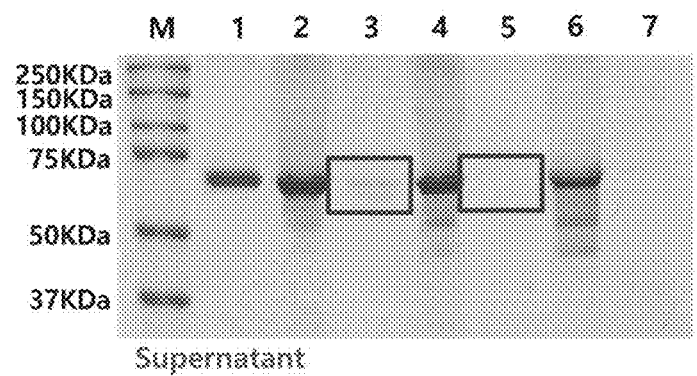
FIG. 2 shows the results of SDS-PAGE of BSA under individual conditions, in which each sample is loaded in an amount of 20 µl per well and the red squares represent BSA encapsulated in each coacervation state.
Figure 2:
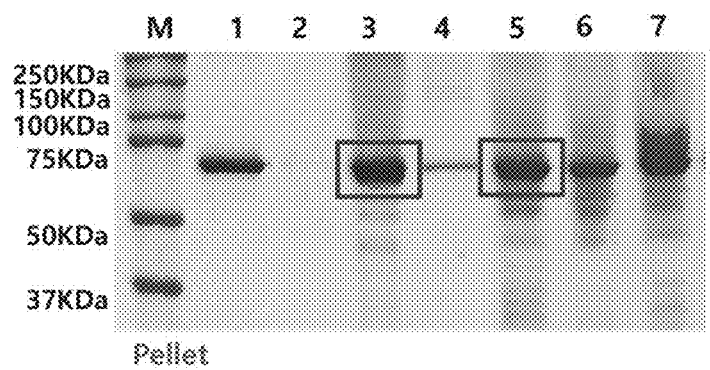

The present disclosure pertains to a coacervate composition containing a protein drug, gelatin A, sodium alginate and an acid.

Coacervation is the spontaneous formation of a high-density liquid phase that forms a macromolecular solution having low solvent affinity from the interaction of complementary macromolecular species (Bohidar, H. B. *Indian*

*Society for Surface Science and Technology* 2008; 24:105-124). For complex coacervation reactions derived from cationic and anionic polymer electrolytes, the pH is adjusted to neutralize each net charge from the polymer-rich liquid.

Complex coacervate is known to have very low interfacial energy in aqueous solutions, thus allowing coacervate to encapsulate various particles in a solution. A coacervate drug delivery system encapsulates a high dose of the drug and is spontaneously formed in an aqueous medium. When a protein drug is encapsulated in coacervate, it may be protected from the external environment and the biological activity thereof may be maintained. Compared to other DDS such as microparticles, coacervate is characterized in that coacervation proceeds rapidly and does not require an organic solvent that may be harmful to a protein drug. Not only a natural polymer but also a synthetic polymer are used for microencapsulation and controlled release of the active ingredient. In recent years, however, a natural polymer is used due to the nontoxicity and biodegradability thereof.

In the present disclosure, gelatin A (GA) and sodium alginate (SA) are used as cationic and anionic polymer electrolytes for complex coacervation. Collagen-derived gelatin has been used in medicaments and pharmaceutical products, and has been used clinically for a long time, proving its safety.

There are two types of gelatin. Gelatin A is derived from acid-cured tissue and has a 78-80 mM free carboxyl group for 100 g of protein and a pI of 7.0-9.0. Gelatin B is derived from lime-cured tissue and has a 100-115 mM free carboxyl group for 100 g of protein and a pI of 4.7-5.2. In the present disclosure, gelatin A is used because the net charge of gelatin should be positive at a low pH of 4 to 5. Sodium alginate (SA) is a high negatively-charged polymer and is widely used in various dosage forms in the pharmaceutical industry.

The acid used in the composition of the present disclosure is a material that dissociates in aqueous solution to produce hydrogen ions and neutralize with a base to form a salt, and any example thereof may be used, so long as it is a typical acid that is used pharmaceutically. Examples thereof may include hydrochloric acid, nitric acid, sulfuric acid, citric acid, acetic acid, and the like, and acetic acid is preferably used, but the present invention is not limited thereto.

In the present disclosure, a coacervate formulation using GA and SA is screened through changes in molecular weight, polymer ratio and reaction pH, whereby the specific coacervate composition of the present disclosure is obtained, and the coacervate system thus obtained is evaluated with regard to physical appearance, uniformity, size distribution, protein encapsulation efficiency and trypsin digestion. In order to evaluate wound closure and long-term stability, EGF-coacervate is lyophilized and used for release and bioactivity tests.

In an embodiment of the present disclosure, gelatin A may have an average molecular weight of 20 to 25 KDa and a gel strength of 90 to 110 g, but the present invention is not limited thereto.

In an embodiment of the present disclosure, gelatin A and sodium alginate may be contained at a weight ratio of 1:0.2 to 1.2, and the acid may be 5.4 to 16.3 mM acetic acid.

In an embodiment of the present disclosure, in the coacervate to composition, the ratio of gelatin A:sodium alginate may correspond to a weight ratio of 1:1 and the acid may be 5.4 to 16.3 mM acetic acid, the ratio of gelatin A sodium alginate may correspond to a weight ratio of 1:0.8 and the acid may be 5.4 to 10.9 mM acetic acid, or the ratio of gelatin A:sodium alginate may correspond to a weight ratio of 1:0.4 and the acid may be 5.4 to 8.2 mM acetic acid, and preferably, the ratio of gelatin A:sodium alginate is a weight ratio of 1:1 and the acid is 16.3 mM acetic acid, or the ratio of gelatin A:sodium alginate is a weight ratio of 1:0.4 and the acid is 8.2 mM acetic acid.

In an embodiment of the present disclosure, the protein drug may be at least one selected from the group consisting of epidermal growth factor (EGF), growth hormone (GH) and fibroblast growth factor (FGF).

In the coacervate composition, the protein drug may be contained in an amount of 100 µg/g to 100 µg/g, and SA may be contained in an amount of 1 to 2.5 mg/g.

In addition, the present disclosure pertains to a wound-healing agent including the coacervate composition.

In an embodiment of the present disclosure, the wound is a chronic intractable wound, which may be a diabetic ulcer, particularly a diabetic foot ulcer.

A better understanding of the present disclosure will be given through the following examples. However, these examples are merely set forth to illustrate the present disclosure, and are not to be construed as limiting the scope of the present disclosure.

Examples

I. Reagent and method
1. Reagent

Gelatin A having gel strength of 300 (high-molecular-weight gelatin A (HWGA) (average molecular weight of 100 KDa)), gelatin A having gel strength of 90-110 (low-molecular-weight gelatin A (LWGA) (average molecular weight of 20-25 KDa)) and trifluoroacetic acid (TFA) were purchased from Sigma-Aldrich (St, Louis, Mo., USA). Sodium alginate (SA), acetic acid and acetonitrile (ACN) were purchased from Daejeong (Gyeonggi-do). Epidermal growth factor (EGF) was supplied from Daewoong Pharmaceutical. A buffer (Dulbecco's phosphate-buffered saline (DPBS)) was purchased from Welgene (Gyeongsangbuk-do), a culture medium (Dulbecco's Modified Eagle Medium, DMEM) was purchased from Hyclone (Logan, USA), and 0.25% trypsin-EDTA and fetal bovine serum (FBS) were purchased from Gibco (Paisley, UK). Human dermal fibroblast (HDP) was purchased from Lonza (Walkersville, USA). Cell counting kit-8 (CCK-8) was purchased from Dojindo (Kumamoto, Japan).

A standard reagent (Precision Plus protein dual color standard), a polyvinylidene fluoride (PVDF) membrane, a 30% acrylamide/Bis solution (29:1), a 10% sodium dodecyl sulfate (SDS) solution, ammonium persulfate (APS), a stacking gel buffer, a resolving buffer, 10× tris/glycine/SDS buffer, 10× tris/glycine buffer, 1.0× tris buffered saline (TBS), and tetramethylethylenediamine (TEMED) were purchased from Bio-Rad (California, USA). Bovine serum albumin (BSA, Millipore, Ill., USA), a 0.2 µm membrane filter (PALL, New York, USA), a bicinchoninic acid (BCA) assay kit and an enhanced chemiluminescence (ECL) western-blotting substrate (Thermo Scientific, Rockford, USA), a silver staining kit (Biosesang, (Iyeonggi-do, South Korea), and a secondary antibody rabbit anti-mouse HRP (Abeam, Cambridge, UK) were purchased.

2. BSA coacervate using HWGA and SA
A. Preparation of BSA-coacervate and measurement of physical properties thereof For the preparation of BSA-coacervate, HWGA, SA and BSA were used. 1% HWGA (w/w, 10 mg/g) and 0.5% SA (w/w, 5 mg/g) were prepared using deionized to water and were used as stock solutions. Specifically, a 543.8 mM acetic acid solution was diluted with deionized water so that the final acetic acid concentration was 0 mM, 1.1 mM or 2.7 mM. Next, the diluted acetic acid solution was added with a 1% HWGA stock solution in a required amount such that the final polymer ratio of coacervate was HWGA:SA=1:0.1, 1:0.125, 1:0.167, or 1:0.25, after which a BSA solution (1 mg/ml) was added such that the final concentration was 1 µg/g. Finally, a 0.5% SA stock solution was added so as to be adapted for a desired HWGA:SA ratio, and was then uniformly mixed. The final polymer concentration in the coacervate sample containing HWGA and SA at various ratios was 9.9, 8.1, 6.3, or 5.4 mg/g.

The state was observed with the naked eye, three ratios (1:0.125, 1:0.167, 1:0.25) at different acetic acid concentrations were applied, the pH was observed using a pH meter (Thermo Scientific, Massachusetts, USA), and the turbidity at 450 nm (Microplate reader, Molecular Devices, California, USA), zeta potential, particle size and PDI (polydispersity index, Zetasizer Nano-ZS, Malvern Instruments, Worcester, UK) were measured.

B. Encapsulation efficiency of BSA-coacervate

BSA-coacervate was separated into a supernatant and a pellet through centrifugation (14000 g, 10 min, 4° C., ×2). These were used for quantitative and qualitative protein analysis. The pellet contained only coacervate, whereas the supernatant was mostly composed of free protein and polymer. The supernatant and the pellet were placed in respective tubes and the pellet was dissolved in PBS having the same volume as the supernatant. Each sample was used for BCA analysis and SDS-PAGE. In order to measure the encapsulation efficiency of BSA-coacervate, samples were analyzed with a quantitative BCA assay kit and detected with a microplate reader at 562 nm. Since BCA analysis was unable to detect each protein concentration, the total amount of BSA-containing protein in each sample was identified. For comparison with the encapsulation efficiency of BSA alone in coacervate under various conditions, 10% SDS PAGE using silver staining was used for qualitative analysis. 20 µl of each sample was mixed with 5× sample buffer (Bio Solution, Seoul, Korea) and denatured at 100° C. for 10 min. The following two processes were then performed: ① application of 80 V for 30 min and ② application of 100 V for 100 min. After completion thereof, silver staining was performed in accordance with the method described in the silver staining kit.

3. EGF-coacervate using HWGA and SA

HWGA, SA and EGF were used for the preparation of EGF-coacervate. In order to measure pH, turbidity, zeta potential, particle size and PDI, samples were prepared under the conditions of three final acetic acid concentrations (0 mM, 1.1 mM, 2.7 mM) and three HWGA:SA ratios (1:0.125, 1:0.167, 1:0.25). Quantitative analysis and qualitative analysis of the supernatant and pellet of EGF-coacervate were performed for two conditions showing good particle quality in BSA-coacervate and high BSA content in the pellet, among various conditions. The above analysis method was the same as in 2.B except for the SDS-PAGE gel %. Here, since EGF has a lower molecular weight (6.4 KDa) than BSA (66 KDa), 15% SDS-PAGE was used.

After analysis, the EGF-coacervate conditions were changed to increase the encapsulation efficiency of EGF. The final polymer concentration was fixed to 5 mg/g, the HWGA:SA ratio was changed to 1:1, 1:0.8, and 1:0.4, and a 543.8 mM acetic acid solution was used in a required amount such that the final acetic acid concentration became 0 mM, 2.7 mM, 5.4 mM, 8.2 mM, 10.9 mM, 13.6 mM and 16.3 mM. In the preparation sequence, in order to fix the same polymer concentration, 543.8 mM acetic acid to was diluted with deionized water such that the final acetic acid concentrations respectively matched the above 7 values, after which 2.5 mg of 0.1% HWGA stock solution was added thereto. Next, the EGF solution (1 mg/ml) was added such that the final concentration was 100 µg/g. Finally, 0.5% SA stock solution was added in an amount of 1 mg, 2 mg or 2.5 mg. The method of measuring physical properties is the same as described in 2.A except for turbidity. Turbidity was measured using a 1 ml disposable cuvette with an ultraviolet spectrophotometer (Shimadzu, Kyoto, Japan).

4. EGF-coacervate using LWGA and SA

A. Physical properties of EGF-coacervate

The conditions of EGF-coacervate using LWGA and SA were the same as the ratio and acetic acid concentration described in section 2.B. After each sample was prepared, the formation of the sample was observed. The method of measuring physical properties is the same as in 2.B.

B. Encapsulation efficiency of selected EGF-coacervate

After analyzing EGF-coacervate using LWGA, the conditions of EGF-coacervate showing an absorbance of 1.5 or more at 450 nm while forming a uniform colloid (PDI of 0.4 or less) were selected. EGF-coacervate under eight conditions was selected for quantitative analysis and qualitative analysis of the supernatant and pellet of EGF-coacervate. The protein quantification method of the supernatant and the pellet was the same as in 3.A. Qualitative analysis of EGF was performed through western blotting. SDS-PAGE was carried out in the same manner as in 3.A, and the protein of an acrylamide gel was transferred on a PVDF membrane at 100 V for 90 min. After blocking with 5% BSA (0.05% Tween20 in TBST buffer-TBS buffer) for 1 hr. at room temperature (RT), the to primary antibody (human EGF antibody) was allowed to bind overnight at 4° C. The membrane was treated with horseradish peroxidase (HRP)-conjugated secondary antibody (rabbit anti-mouse HRP) for 1 hr at RT. The labeled protein bands were allowed to react with an ECL western-blotting substrate and measured using an image analyzer (ImageQuant LAS 4000; GE Healthcare, Little Chalfont, UK).

C. Preparation of GH-coacervate and FGF-coacervate

For growth hormone (GH) and fibroblast growth factor (FGF), each sample was prepared using the above composition, after which the formation of the sample was observed and the physical properties thereof were measured.

5. Trypsin digestion test of optimized EGF-coacervate

EGF-coacervate using LWGA, selected based on the results of the encapsulation efficiency of EGF in the pellet, was prepared under the following optimized conditions, and a trypsin digestion test was performed.

(1) Free EGF (10 µg of EGF)
(2) 1:1 EGF-mixture (10 µg of EGF, 250 µg of LWGA, 250 µg of SA, acetic acid not added) [Comparative Example 1]
(3) 1:1 EGF-coacervate (10 µg of EGF, 250 µg of LWGA, 250 µg of SA, 16.3 mM acetic acid) [Example 1]
(4) 1:0.4 EGF-mixture (10 µg of EGF, 250 µg of LWGA, 100 µg of SA, acetic acid not added) [Comparative Example 2]
(5) 1:0.4 EGF-coacervate (10 g of EGF, 250 µg of LWGA, 100 µg of SA, 8.2 mM acetic acid) [Example 2]

The sample was placed in a tube and centrifuged. 0.04% trypsin-EDTA was added to the sample, followed by incubation with 0.04% trypsin-EDTA at 37° C. for 1 hr or 2 hr. Qualitative analysis of EGF remaining in the digestion solution was performed in the same manner as the western blotting performed in 4.B.

6. Preparation of lyophilized sample

Lyophilization was performed in order to improve wound closure and long-term storability. After preparation of the lyophilized sample, an in-vitro release test and a bioactivity test were performed to measure the release pattern and bioactivity of EGF-coacervate.

A. Preparation of sample for in-vitro release test

EGF-mixture and EGF-coacervate were prepared using LWGA:SA at 1:0.4 (2.5 mg of LWGA, 1 mg of SA and 100 μg of EGF) in the absence of acetic acid and in the presence of 8.2 mM acetic acid. After lyophilization, they were stored at −80° C.

B. Preparation of sample for in-vitro cell proliferation and migration test

LWGA:SA-1:1 mixture (250 g of LWGA, 250 μg of SA, acetic acid not added), LWGA:SA-1:1 coacervate (250 μg of LWGA, 250 μg of SA, 16.3 mM acetic acid). LWGA:SA-1:0.4 mixture (250 μg of LWGA, 100 μg of SA, acetic acid not added) and LWGA:SA-1:0.4 coacervate (250 μg of LWGA, 100 μg of SA, 8.2 mM acetic acid); LWGA:SA-1:1 EGF-mixture (10 ng of EGF, 250 μg of LWGA, 250 μg of SA, acetic acid not added) [Comparative Example 1], LWGA:SA-1:1 EGF-coacervate (10 ng of EGF, 250 μg of LWGA, 250 μg of SA, 16.3 mM acetic acid) [Example 1], LWGA:SA-1:0.4 EGF mixture (10 ng of EGF, 250 μg of LWGA, 100 μg of SA, acetic acid not added) [Comparative Example 2] and LWGA:SA-1:0.4 EGF-coacervate (10 ng of EGF, 250 μg of LWGA, 100 μg of SA, 8.2 mM acetic acid) [Example 2] were added to respective wells of a 96-well plate. Thereafter, each sample was frozen at −80° C. The frozen sample was lyophilized in a freeze dryer (Operon, Gyeonggi-do, Korea). The lyophilized sample was stored at −20° C. until use.

C. Preparation of sample for in-vivo test

LWGA:SA-1:0.4 EGF-mixture (1 μg of EGF, 250 μg of LWGA, 100 μg of SA, acetic acid not added) [Comparative Example 2] and LWGA:SA-1:0.4 EGF-coacervate (1 μg of EGF, 250 μg of LWGA, 100 μg of SA, 8.2 mM acetic acid) [Example 2] were added to respective wells of a 96-well plate. Thereafter, each sample was frozen at −80° C. The frozen sample was lyophilized in a freeze dryer. The lyophilized sample was stored at −20° C. until use.

7. In-vitro release test

Each sample was placed in a Transwell insert, 70 μl of DW was added for sample hydration, and 700 μl of DPBS was placed in a 24-well plate. 70 μl of a 1 mg/g EGF solution was placed in the Transwell insert, which was then placed in the 24-well plate containing 700 μl of DPBS. Samples were prepared at each sampling time point (1, 2, 4, 6 and 8 hr), and were then incubated at 32° C. and 150 rpm. After each sampling time point, the release medium was transferred from the 24-well plate to an E-tube and stored at 4° C. until termination. After completion of release, EGF in the sample was tittered with a 0.45 μm syringe filter, followed by high-performance liquid chromatography (HPLC, Knauer, Berlin, Germany) and calculation using HPLC columns (00G-4167-E0 Jupiter 5 μm C4 300A 250×4.6 mm, Phenomenex, Torrance, USA). The mobile phase was used by mixing solution A (0.1% TFA in DW) and solution B (0.1% TFA in MN).

8. Ire vitro cellular activity study

A. Analysis of cell proliferation

Human dermal fibroblasts (HDFs) for comparing cell proliferation and migration capacity were cultured in DMEM containing 10% FBS. The cells were cultured in 100-π dishes for six subculture cycles until reaching 80% confluence. The cells were separated using 0.25% trypsin-EDTA and then seeded at $1 \times 10^4$ cells per well into a 24-well plate. The cells were incubated at 37° C. for 24 hr. Thereafter, the medium was replaced with 800 μl of DMEM containing 1% FBS per well, except for the following groups [positive control (1 ml of 10% FBS), negative control (1 ml of 1% FBS), and EGF (1 ml of 10 ng/ml EGF in 1% FBS)]. The lyophilized sample was placed in a Transwell insert, and 200 μl of a medium containing 1% FBS was added to the insert. The insert was placed in the well and then incubated at 37° C. for 48 hr. The proliferation of HDF was measured through CCK-8 analysis. All results were measured at 450 nm and normalized to the negative control.

B. Analysis of cell migration

HDF was cultured in 100-π dishes for seven subculture cycles until reaching 80% confluence. After marking the center of the well in a 24-well plate, a 0.1% gelatin solution was added thereto. The plate was incubated at 37° C. for 2 hr and then washed once with DPBS to prepare a 24-well plate coated with gelatin. The cells were separated using 0.25% trypsin-EDTA, and then the coated plate was seeded with $9 \times 10^4$ cells per well. The cells were incubated overnight at 37° C. The cells were scratched using a 200-μl pipette tip and the well was washed two times with DPBS in order to remove debris. 1 ml of a medium containing 0.5% FBS was added per well, and photographs were taken using a microscope (Leica Wetzlar, Germany) in order to measure the time of scratch (0 hr). The medium was replaced with 800 μl of a medium containing 0.5% FBS per well, except for the following groups [positive control (1 ml of 10% FBS DMEM), negative control (1 ml of 0.5% FBS DMEM), and EGF (1 ml of 10 ng/ml EGF in 0.5% FBS DMEM)]. The lyophilized sample was placed in a Transwell insert, and 200 μl of DMEM containing 1% FBS was added to the insert. The cells were incubated at 37° C. for 8 hr and the scratched portions were then photographed. Scratch width was measured using Image-Pro Plus software (Media Cybernetics, USA) and was calculated using the following Equation 1.

Wound area ratio=$\{(A_0-A_t)/A_0\}$/result value of negative control (in which $A_0$ is the original wound area and $A_t$ is the wound area after 8 hr.) [Equation 1]

9. In-vivo study

A. Streptozotocin (STZ)-induced diabetic mouse model

Six-week-old male C57BL/6 mice (n=5 in most comparative groups) were used for the experiment. All animal experiments were performed in accordance with the regulations of the Institutional Animal Care and Use Committee (IACUC No: 170028) of CHA University. All mice were allowed to acclimate to the environment of a well-ventilated room for a week before the experiment. After starving for 12-14 hr before administration with streptozocin (Tocris, Bristol, UK), the mice were subjected to intraperitoneal injection two times with 100 mg/kg of streptozocin (Tocris, Bristol, UK) in 100 mM citrate buffer (pH 4.5) to induce STZ diabetes, and were then starved for 12 hr. Blood glucose levels after STZ treatment were measured every 3-4 days using an Accu-check active kit (Roche, Basel, Switzerland). In general, mice having blood glucose levels higher than 250 mg/dl are used as diabetes-induced models. Accordingly, in this experiment, mice with blood glucose levels of 250 mg/dl or more 2 weeks after treatment with a certain amount of STZ were selected and used for wound-healing evaluation.

B. Analysis of mouse skin wound healing

Experimental animals were divided into five groups: group 1 (normal) as a control (mice without diabetes), group 2 (negative control), group 3 (free EGF), group 4 (1:0.4

EGF-mixture), and group 5 (1:0.4 EGF-coacervate) as a diabetic mouse group. Under mild anesthesia through intraperitoneal administration with a ketamine/rompun (3:1) cocktail, the washed back skin of six mice was shaved and wiped with 70% ethanol. Thereafter, a wound (full-thickness wound, diameter of 5 mm) was formed on the back of each mouse using a biopsy punch (Kai Medical, Oyana, Japan). Group 1 (normal) and group 2 (negative) were treated with DPBS as controls. Group 3 was administered with 1 μg/10 μl of free EGF. Group 4 was administered with lyophilized LWGA:SA-1:0.4 EGF-mixture. Group 5 was administered with lyophilized LWGA:SA-1:0.4 EGF-coacervate. In groups 1, 2 and 3, 10 μl of each sample was applied to the wound. In groups 4 and 5, each lyophilized sample was applied to the wound and 5 μl of DW was added for sample hydration. The wound was treated two times (0 days, 3 days) with the sample. Each mouse was kept in a separate room with food and water. In order to calculate the wound closure rate based on the wound area a wound photograph was taken at each time point (0, 3, 5, 7, 10, 12, and 14 days) after surgery. The wound area was calculated using the following Equation 2.

Wound area (%)=$\{(A_0-A_t)/A_0\} \times 100$ (in which $A_0$ is the original wound area and $A_t$ is the wound area at each time point.)   [Equation 2]

Results

I. Interaction between HWGA, SA and BSA

A. Physical properties of BSA-coacervate

The ratio of gelatin A and sodium alginate was set to 1:0.25 (HWGA:SA-1:0.25) and the experiment was started. Reducing pH at the same polymer ratio increased turbidity and formed uniform coacervate. The pH, which forms coacervate without causing precipitation, was defined as $pH_c$. However, as the proportion of SA decreased, a solid precipitate phase rather than a liquid coacervate phase appeared at the same acetic acid concentration. In the precipitate phase, heterogeneous particles appeared in an aggregated form (FIG. 1).

In the groups other than HWGA:SA-1:0.1, zeta potential, particle size and PDI, used for panicle quality evaluation, were measured, and the results thereof are shown in Table 1 below. As shown in Table 1, the lower the proportion of SA and pH, the closer the zeta potential to zero and the larger the particle size. Here, when the PDI was measured below 0.4, uniform coacervate was formed.

B. Encapsulation efficiency of BSA-coacervate

Based on the results of quantitative protein analysis using a BCA assay method, the higher the acetic acid concentration, the higher the protein content of the pellet at each ratio compared to the supernatant (Table 2). In SDS-PAGE, coacervate having PDI less than 0.4 and turbidity of 1 or more (HWGA:SA-1:0.25, 2.7 mM acetic acid and HWGA:SA-1:0.167, 2.7 mM acetic acid) exhibited higher encapsulation efficiency than others. The HWGA:SA-1:0.125, 2.7 mM acetic acid sample also exhibited high encapsulation efficiency, but was a solid precipitate (FIG. 2).

TABLE 2

| | HWGA:SA Ratio | | | | | |
|---|---|---|---|---|---|---|
| | 1:025 | | 1:0.167 | | 1:0125 | |
| Acetic acid (nM) | 1.1 | 2.7 | 1.1 | 2.7 | 1.1 | 2.7 |
| Pellet protein (%) | 2.46 | 78.71[a] | 11.83 | 93.16[c] | 72.19 | 95.21 |
| Supernatant protein (%) | 90.55 | 34.53 | 91.01 | 18.69 | 47.48 | 10.50 |

[a]Relative to total protein content (BSA + gelatin).
[c]$pH_c$ at which coacervation occurs at each reaction condition 2. Interaction between HWGA, SA and EGF A. Low encapsulation efficiency of EGF under conditions the same as for BSA-coacervate Under the same conditions as the BSA-coacervate system, the physical properties of EGF-coacervate were similar to those of BSA-coacervate. Reducing pH at the same polymer ratio increased turbidity and formed uniform coacervate. However, lowering the proportion of SA at the same acetic acid concentration resulted in the formation of a solid-precipitate phase rather than a liquid-coacervate phase. The lower the proportion of SA and pH, the closer the zeta potential to zero and the larger the particle size. Turbidity of 1 or more and PDI of 0.4 or less were identical to the conditions of BSA-coacervate showing uniform and high encapsulation efficiency (Table 3). The results of measurement of HWGA and SA having an EGF composite phase are shown in Table 3 below.

TABLE 1

| | HWGA:SA Ratio | | | | | | | | |
|---|---|---|---|---|---|---|---|---|---|
| | 1:0.25 | | | 1:0.167 | | | 1:0.125 | | |
| Acetic acid (nM) | 0 | 1.1 | 2.7 | 0 | 1.1 | 2.7 | 0 | 1.1[a] | 2.7[b] |
| Turbidity | 0.01 | 0.01 | 1.07 | 0.01 | 0.01 | 1.65 | 0.01 | 1.30 | — |
| pH | 6.10 | 5.13 | 4.81[c] | 6.01 | 5.26 | 4.89[c] | 5.96 | 5.30 | 4.96 |
| Zeta potential | −27.4 | −22.4 | −21.6 | −24.5 | −18.8 | −12.4 | −16.90 | −12.7 | — |
| Particle size | 500.2 | 108.3 | 314.5 | 510.8 | 669.2 | 574.2 | 816.7 | 1306.5 | — |
| PDI | 0.911 | 0.978 | 0.135 | 0.778 | 1 | 0.359 | 0.825 | 1 | — |

[a]The reaction mixture becomes turbid with some large particles
[b]Extensive aggregation
[c]$pH_c$ at which coacervation occurs at each reaction condition

TABLE 3

| | HWGA:SA Ratio | | | | | | | | |
|---|---|---|---|---|---|---|---|---|---|
| | 1:0.25 | | | 1:0.167 | | | 1:0.125 | | |
| Acetic acid (nM) | 0 | 1.1 | 2.7 | 0 | 1.1 | 2.7 | 0 | 1.1[a] | 2.7[b] |
| Turbidity | 0.01 | 0.01 | 1.34[c] | 0.01 | 0.01 | 1.71[c] | 0.01 | 1.24 | — |
| pH | 6.12 | 5.11 | 4.74 | 6.07 | 6.20 | 4.86 | 5.94 | 6.27 | 4.91 |
| Zeta potential | −34.2 | −27.0 | −21.4 | −20.6 | −18.0 | −14.5 | −16.5 | −15.4 | — |
| Particle size | 380.3 | 174.9 | 371.0 | 497.6 | 514.7 | 683.3 | 704.5 | 1333.0 | — |
| PDI | 0.913 | 0.965 | 0.200 | 0.738 | 1 | 0.395 | 0.776 | 0.570 | — |

Figure 3:
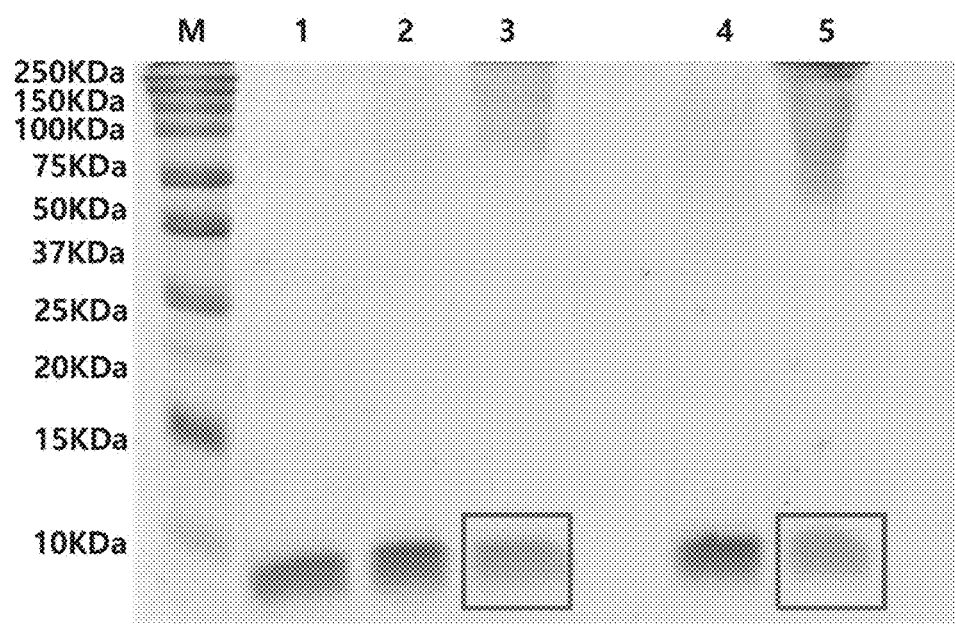
FIG. 3 shows the results of SDS-PAGE of EGF under individual conditions, in which the sample is loaded in an amount of 20 µl per well.

[a]The reaction mixture becomes turbid with some large particles
[b]Extensive aggregation
[c]$pH_c$ at which coacervation occurs at each reaction condition Among the experimental conditions, two conditions ([HWG-A:SA-1:0.25, 2.7 mM acetic acid] and [HWFA:SA-1:0.167, 2.7 mM acetic acid]) were selected in order to measure the encapsulation efficiency of EGF. The total protein content in the pellet measured by BCA analysis was 76.06% and 80.59% for HWGA:SA-1:0.25, 2.7 mM acetic acid and HWGA:SA-1:0.167, 2.7 mM acetic acid, respectively (Table 4). However, the results of SDS-PAGE showed that EGF in the pellet was lower than in the supernatant (FIG. 3). Table 4 below shows the results of BCA analysis of protein under individual conditions.

TABLE 4

| | HWGA:SA Ratio | |
|---|---|---|
| | 1:0.25 | 1:0.167 |
| Supernatant protein (%)[a] | 39.58 | 26.78 |
| Pellet protein (%)[a] | 70.00[c] | 80.59[c] |

[a]Relative to total protein content (BSA + gelatin)
[c]$pH_c$ at which coacervation occurs at each reaction condition B. HWGA- and SA-based modified coacervate formulation including EGF In order to evaluate the formation of coacervate in a wider range, the ratio of HWGA and SA was fixed to 1:1, 1:0.8 and 1:0.4, and the acetic acid concentration was set to 0 mM, 2.7 mM, 5.4 mM, 8.2 mM, 10.9 mM, 13.6 mM and 16.3 mM. In order to determine the optimal conditions of EGF-coacervate, turbidity, zeta potential, particle size and PDI under individual conditions were measured and evaluated. In order to optimize the physical properties of HWGA:SA coacervate, HWGA and SA were tested at different acetic acid concentrations. The 0 mM acetic acid group with almost zero turbidity was a clear solution. In HWGA:SA-1:1, 5.4 mM, HWGA:SA-1:0.8, 5.4 mM, and HWGA:SA-1:0.4, 2.7 mM, a uniform suspension was observed. However, all of the other samples were aggregated, and the respective PDIs thereof were higher than 0.4 (Table 5). In order to optimize coacervate conditions for obtaining uniform coacervate and high encapsulation efficiency of EGF over a wider range, other factors in addition to the polymer ratio and pH should be considered. Table 5 below shows the results of measurement of modified formulations using HWGA and SA. They were prepared at various polymer ratios and acetic acid concentrations.

TABLE 5

| HWGA:SA 1:1 | | | | | | | |
|---|---|---|---|---|---|---|---|
| Acetic acid (nM) | 0 | 2.7 | 5.4[c] | 8.2 | 10.9 | 13.6 | 16.3 |
| pH | 6.23 | 4.84 | 4.58 | 4.42 | 4.30 | 4.21 | 4.14 |
| Turbidity | 0.05 | 0.13 | 1.62 | 1.90 | 1.97 | 1.97 | 1.91 |
| Zeta potential | −62.73 | −38.90 | −39.37 | −37.40 | −36.63 | −41.93 | −39.47 |
| Z-average (d_nm) | 563.10 | 375.43 | 722.53 | 2315.33 | 1114.67 | 1158.87 | 1272.67 |
| PDI | 1 | 0.98 | 0.28 | 0.65 | 0.60 | 0.58 | 0.44 |
| HWGA:SA 1:0.8 | | | | | | | |
| Acetic acid (nM) | 0 | 2.7 | 5.4[c] | 3.2 | 10.9 | 13.6 | 16.3 |
| pH | 6.10 | 4.83 | 4.57 | 4.40 | 4.29 | 4.21 | 4.14 |
| Turbidity | 0.04 | 0.12 | 1.66 | 1.93 | 2.02 | 1.99 | 1.98 |
| Zeta potential | −52.70 | −39.30 | −37.03 | −36.63 | −38.63 | −39.13 | −38.03 |
| Z-average (d_nm) | 561.77 | 328.03 | 641.07 | 1090.00 | 730.33 | 921.73 | 967.33 |
| PDI | 1 | 1 | 0.18 | 0.48 | 0.42 | 0.74 | 0.56 |
| HWGA:SA 1:0.4 | | | | | | | |
| Acetic acid (nM) | 0 | 2.7[c] | 5.4 | 8.2 | 10.9 | 13.6 | 16.3 |
| pH | 5.97 | 4.32 | 4.55 | 4.36 | 4.26 | 4.17 | 4.09 |
| Turbidity | 0.03 | 1.68 | 2.09 | 2.00 | 1.99 | 1.90 | 1.73 |

TABLE 5-continued

| | | | | | | | |
|---|---|---|---|---|---|---|---|
| Zeta potential | −51.60 | −26.80 | −30.07 | −27.30 | −26.05 | −34.33 | −23.47 |
| Z-average (d_nm) | 521.50 | 726.60 | 2130.67 | 3650.00 | 7481.00 | 1474.33 | 2373.33 |
| PDI | 0.85 | 0.38 | 1 | 1 | 0.73 | 0.63 | 0.84 |

$^c$pH$_c$ at which coacervation occurs at each reaction condition

The formulations were prepared at various polymer ratios and acetic acid concentrations. The conditions of uniform coacervate (PDI of 0.4 or less) and high turbidity (1.5 or more) are indicated in bold.

3. EGF-coacervate formulation using LWGA

A. Evaluation of uniform EGF-coacervate using LWGA

Figure 4:
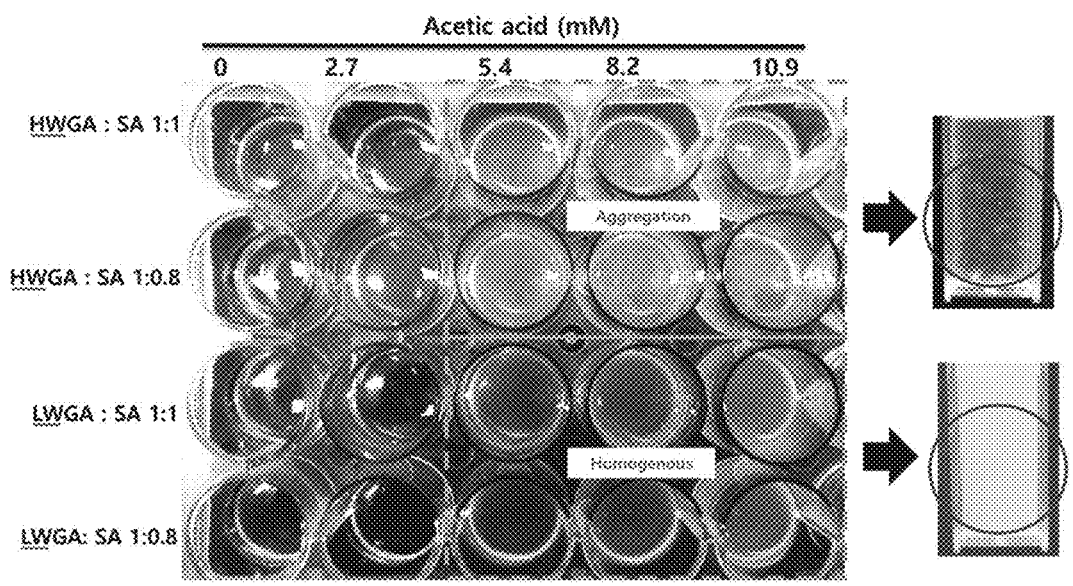
FIG. 4 shows the results of comparison of composites using high-molecular-weight gelatin A (HWGA) and low-molecular-weight gelatin A (LWGA), particularly the results of observation of the polymer composites of mixtures prepared at various polymer ratios and acetic acid concentrations.
Figure 5:
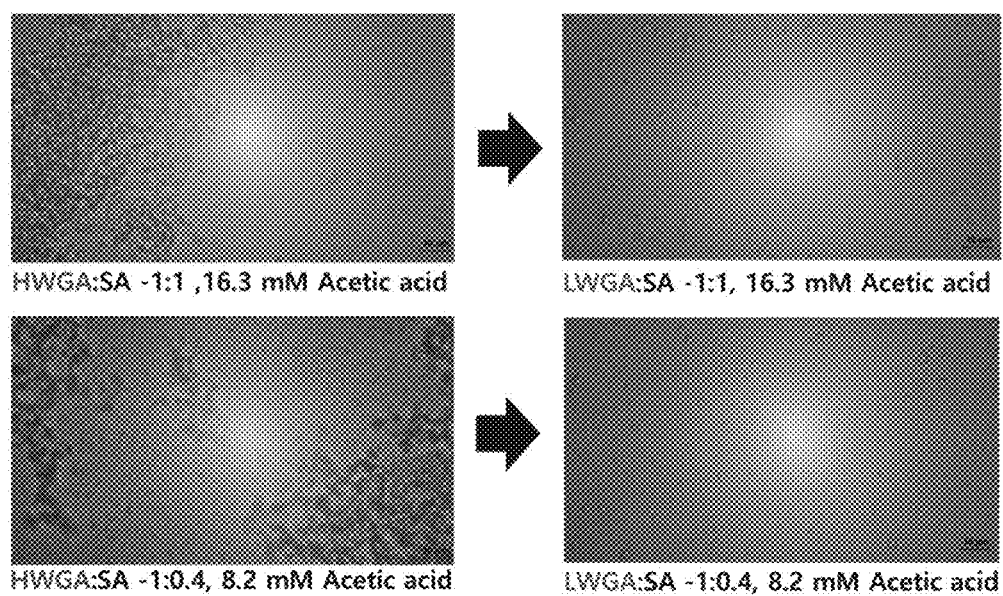
FIG. 5 shows images of an aggregate formed with HWGA:SA and a uniform colloid formed with LWGA:SA (3400×, bars=10 µm) using an optimal microscope (Sometech, Seoul, Korea)

In order to determine the conditions for forming coacervate in a wider range, coacervate was prepared using low-molecular-weight gelatin A (gel strength of 90-110 (about 20-25 KDa), LWGA) instead of HWGA The concentration conditions using LWGA and SA are the same as described in 2.B. The results of observing the polymer composites of the mixtures prepared at various polymer ratios and acetic acid concentrations are shown in FIG. 4. As shown in FIG. 4, it can be confirmed that the use of LWGA and SA produces liquid coacervate under certain conditions that form a solid precipitate when using HWGA and SA. Moreover, optical micrographs of the aggregate formed of HWGA:SA and the uniform colloid formed of LWGA:SA are shown in FIG. 5.

Among various conditions, uniform and high-turbidity coacervate with PDI of 0.4 or less and turbidity of 1.5 or more was selected as coacervate having superior properties. The lower the pH, the closer the zeta potential to zero (Table 6). Based on these results, quantitative and qualitative analyses were performed to determine the encapsulation efficiency of EGF under selected conditions. The results of measurement of the modified formulations using LWGA and SA are shown in Table 6 below.

TABLE 6

| LWGA:SA 1:1 | | | | | | | |
|---|---|---|---|---|---|---|---|
| Acetic acid (nM) | 0 | 2.7 | 5.4$^c$ | 8.2$^c$ | 10.9$^c$ | 13.6$^c$ | 16.3$^c$ |
| pH | 6.00 | 4.82 | 4.55 | 4.38 | 4.31 | 4.22 | 4.14 |
| Turbidity | 0.04 | 0.06 | 1.25 | 1.78 | 1.87 | 1.90 | 1.94 |
| Zeta potential | −42.13 | −35.70 | −36.23 | 37.30 | 35.80 | 36.63 | 35.70 |
| Z-average (d_nm) | 334.17 | 527.27 | 864.17 | 807.87 | 639.17 | 955.00 | 914.13 |
| PDI | 0.95 | 0.77 | 037 | 0.31 | 0.21 | 0.39 | 0.30 |
| LWGA:SA 1:0.8 | | | | | | | |
| Acetic acid (nM) | 0 | 2.7 | 5.4$^c$ | 8.2$^c$ | 10.9$^c$ | 13.6 | 16.3 |
| pH | 6.06 | 4.82 | 4.53 | 4.39 | 4.27 | 4.20 | 4.12 |
| Turbidity | 0.04 | 0.07 | 1.43 | 1.82 | 1.86 | 1.88 | 1.97 |
| Zeta potential | −41.30 | −36.80 | −36.40 | −34.23 | −35.90 | −25.53 | −25.87 |
| Z-average (d_nm) | 497.30 | 693.13 | 673.27 | 601.33 | 659.93 | 1112.23 | 5348.67 |
| PDI | 0.76 | 0.68 | 0.30 | 0.25 | 0.21 | 0.49 | 0.40 |
| LWGA:SA 1:0.4 | | | | | | | |
| Acetic acid (nM) | 0 | 2.7$^c$ | 5.4$^c$ | 8.2$^c$ | 10.9 | 13.6 | 16.3 |
| pH | 6.06 | 4.78 | 4.52 | 4.34 | 4.25 | 4.14 | 4.07 |
| Turbidity | 0.03 | 1.32 | 1.91 | 2.01 | 1.97 | 1.88 | 1.69 |
| Zeta potential | −34.97 | −25.00 | −24.37 | −22.30 | −22.27 | −21.57 | −16.47 |
| Z-average (d_nm) | 699.27 | 923.60 | 364.40 | 1191.00 | 2686.67 | 2422.67 | 1810.67 |
| PDI | 0.94 | 0.50 | 0.14 | 0.33 | 0.94 | 0.59 | 0.49 |

$^c$pH$_c$ at which coacervation occurs at each reaction condition

The formulations were prepared at various polymer ratios and acetic acid concentrations. The conditions of uniform coacervate (PDI of 0.4 or less) and high turbidity (1.5 or more) are indicated in bold, B. High encapsulation efficiency of EGF-coacervate under selected conditions In order to measure encapsulation efficiency, eight conditions with PID of 0.4 and turbidity of 1.5 or more (LWGA:SA-1:1, 8.2 mM, 10.9 mM, 13.6 mM, 16.3 mM acetic acid, LWGA:SA-1:0.8, 8.2 mM. 10.9 mM acetic acid, and LWGA:SA-1:0.4, 5.4 mM, 8.2 mM acetic acid) were selected. In BCA analysis, higher acetic acid concentrations (lower pH) resulted in higher protein encapsulation efficiency in each pellet (Table 7). The results of quantitative analysis of EGF based on BCA analysis are shown in Table 7 below.

TABLE 7

| | LWGA:SA Ratio | | | | | | | |
|---|---|---|---|---|---|---|---|---|
| | 1:1 | | | | 1:0.8 | | 1:0.4 | |
| Acetic acid (nM) | 8.2 | 10.9 | 13.6 | 16.3 | 8.2 | 10.9 | 5.4 | 8.2 |
| Supernatant protein (%)$^a$ | 57.79 | 43.99 | 37.02 | 30.67 | 48.63 | 35.83 | 44.97 | 31.06 |
| Pellet protein (%) | 60.96 | 77.24 | 83.51 | 86.37 | 69.17 | 80.57 | 75.83 | 86.73 |

$^a$Relative to total protein content (BSA + gelatin).

Figure 6A:
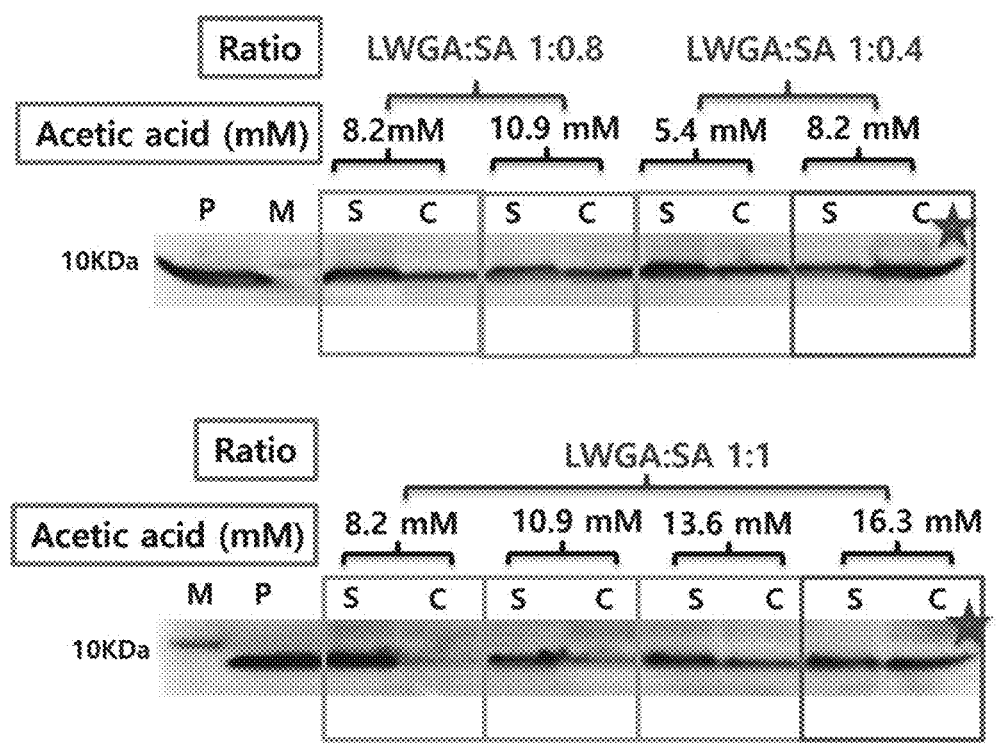
FIGS. 6A, 6B, and 6C show the results of qualitative analysis of protein through western blotting [EGF (FIG. 6A), GH (FIG. 6B), FGF (FIG. 6C)], in which each sample is loaded in an amount of 20 µl per well (P:100 µg/ml free EGF, M: marker, S: coacervate-supernatant, C: coacervate-pellet)

Qualitative analysis of EGF through western blotting showed that the higher the acetic acid concentration, the higher the encapsulation efficiency of EGF in each pellet. In the LWGA:SA-1:1 formulation, the encapsulation efficiency of EGF was the highest under conditions of 16.3 mM acetic acid, and in the LWGA:SA-1:0.8 and LWGA:SA-1:0.4 formulations, the conditions of LWGA:SA-1:0.4 and 8.2 mM acetic acid were excellent in encapsulation efficiency (FIG. 6A).

C. Physical properties of GH-coacervate and encapsulation efficiency

Coacervate was prepared using growth hormone (GH), and the formation thereof and the results of measurement of physical properties thereof are shown in Table 8 below.

naked eye, had a poor PDI value, and had a measured Z-average size of roughly 2399.7. The turbidity was lower than those of other samples because the precipitate settled.

However, LWGA:SA=1:0.4 (acetic acid: 5.4, 8.2 mM), LWGA:SA=1:0.8 (acetic acid: 8.2, 10.9 mM), and LWGA:SA=1:1 (acetic acid: 13.6, 16.3 mM) exhibited turbidity of 1.5 or more and PDI of 0.4 or less, indicating that a large amount of coacervate was homogeneously prepared in the form of nano-sized particles.

Figure 6B:
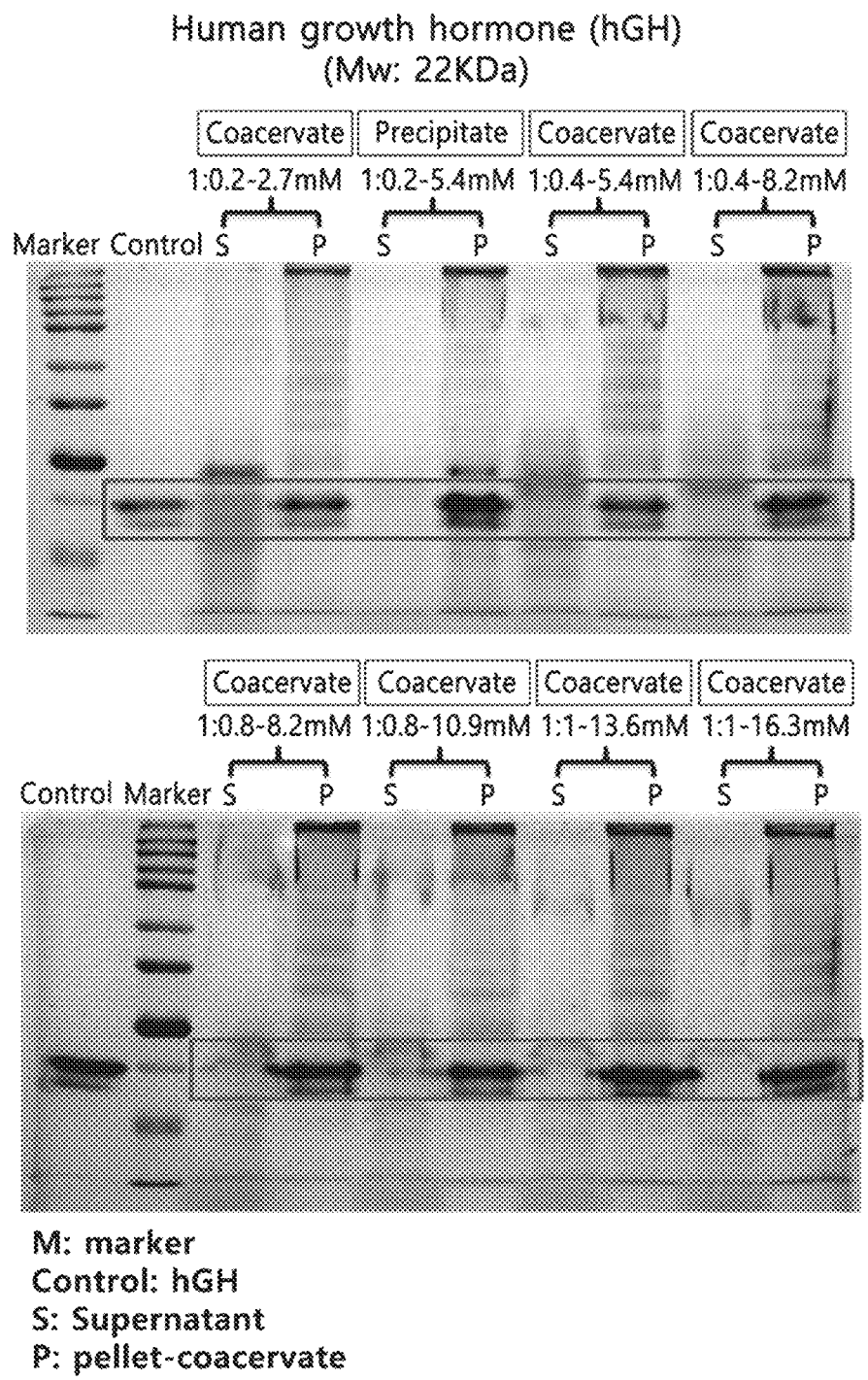

Based on the results of measurement of the encapsulation efficiency of growth hormone (GH), it was confirmed that GH was captured well by coacervate in all ranges (FIG. 6B).

D. Physical properties of FGF-coacervate

Coacervate was prepared using fibroblast growth factor (FGF), and the formation thereof and the results of measurement of physical properties thereof are shown in Table 9 below.

TABLE 9

| | LWGA:SA Ratio | | | |
|---|---|---|---|---|
| | 1:1 | | | 1:0.8 |
| Acetic acid (mM) | 2.2 | 3.3 | 4.4 | 2.4 |
| pH | 4.84 | 4.69 | 4.59 | 4.79 |
| Turbidity (450 nm) | 1.375 | 1.610 | 1.740 | 1.586 |
| Zeta potential | −34.57 | −27.17 | −33.93 | −27.03 |
| Z-average (d, nm) | 1822.7 | 2095.0 | 1609.3 | 3512.3 |
| PDI | 0.294 | 0.257 | 0.254 | 0.322 |

As is apparent from Table 9, in the case of bFGF, coacervate was formed only in LWGA:SA=1:1, 1:0.8, and

TABLE 8

| | Ratio | | | | | | | |
|---|---|---|---|---|---|---|---|---|
| Visual | LWGA:SA = 1:0.2 | | LWGA:SA = 1:0.4 | | LWGA:SA = 1:0.8 | | LWGA:SA = 1:1 | |
| observation | Coacervate | Precipitate | Coacervate | Coacervate | Coacervate | Coacervate | Coacervate | Coacervate |
| Acetic acid (mM) | 2.7 | 5.4 | 5.4 | 8.2 | 8.2 | 10.9 | 13.6 | 16.3 |
| pH | 4.90 | 4.66 | 4.76 | 4.58 | 4.57 | 4.47 | 4.37 | 4.29 |
| Z-average (d_nm) | 721.7 | 2399.7 | 637.1 | 711.2 | 670.8 | 754.1 | 656.9 | 510.7 |
| PDI | 0.581 | 0.456 | 0.366 | 0.191 | 0.216 | 0.281 | 0.213 | 0.146 |
| Zeta potential | −15.30 | −12.17 | −25.17 | −13.4 | −33.73 | −28.80 | −35.27 | −36.20 |
| Turbidity | 1.676 | 0.956 | 1.936 | 1.956 | 1.944 | 1.987 | 1.896 | 2.016 |

As is apparent from Table 8, the LWGA:SA=1:0.2 (2.7 mM acetic acid) formulation appeared homogeneous with the naked eye, but the PDI value was determined to be 0.4 or higher, confirming that it is polydisperse (experimentally estimated).

The LWGA.:SA=1:0.2 (5.4 mM acetic acid) formulation was not homogeneous, aggregated to an extent visible to the the physical properties and encapsulation efficiency were measured in four homogeneous ranges forming coacervate.

Figure 6C:
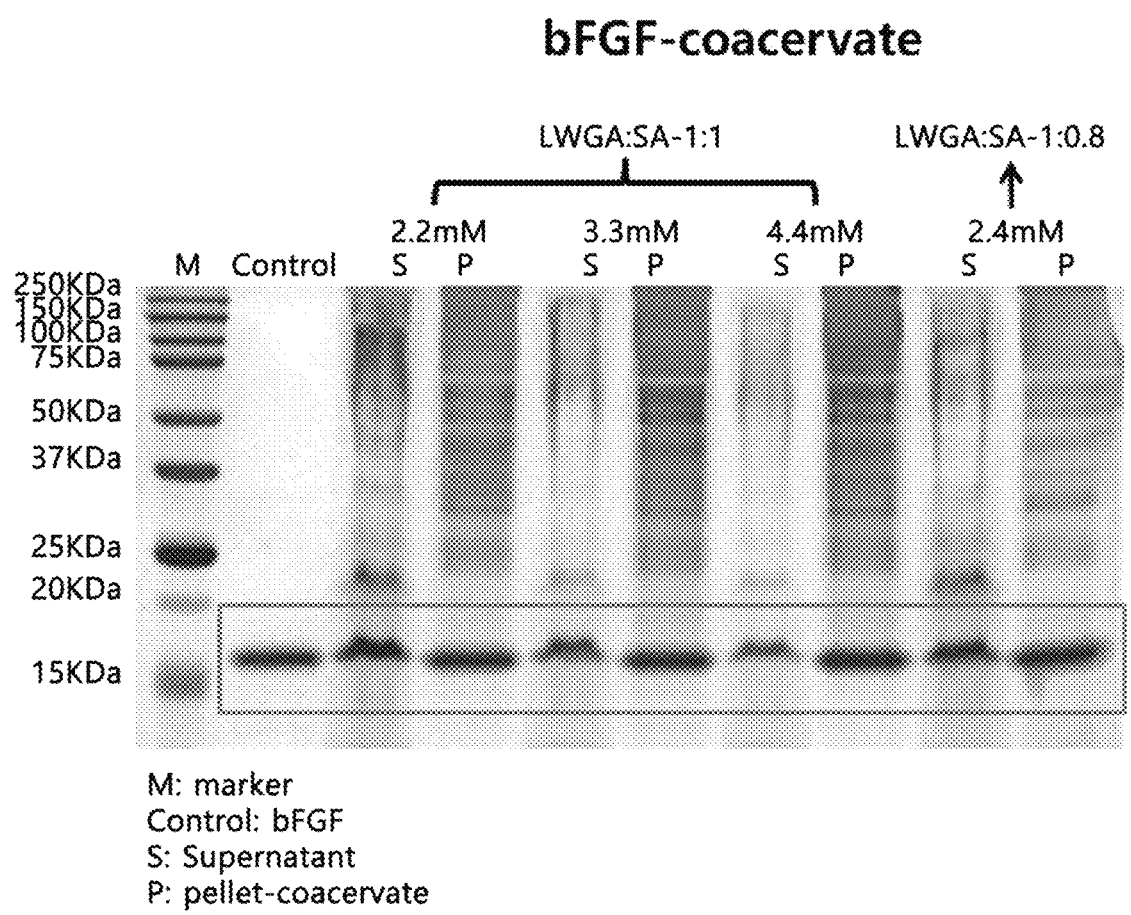

Based on the results of measurement of encapsulation efficiency of FGF, to the higher acetic acid concentration at LWGA:SA=1:1 resulted in higher capture capacity of coacervate, and FGF was captured at a level up to 70-80%, similarly to EGF (1:1-4.4 mM) (FIG. 6C).

4. Evaluation of protective efficacy of EGF from trypsin digestion

Figure 7:
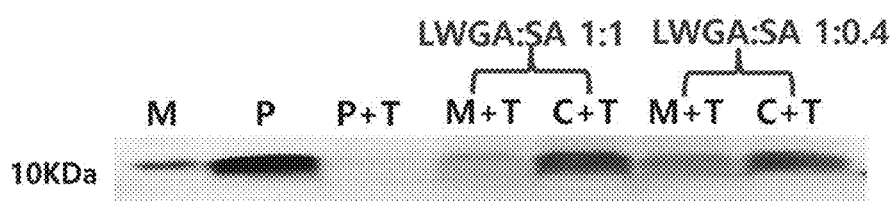
FIG. 7 shows the results of a trypsin digestion test through western blotting (P: free EGF, T: trypsin-EDTA, M: EGF-mixture, C: EGF-coacervate)
Figure 7:
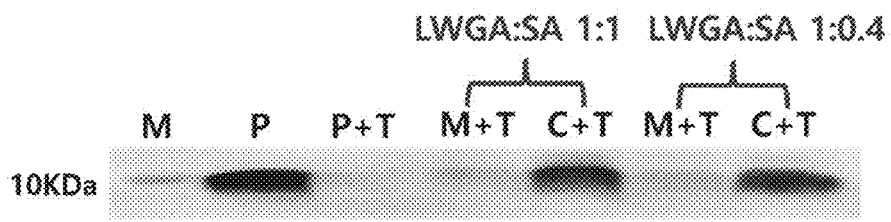

Among the eight conditions, two conditions with relatively high encapsulation efficiency of EGF (LWGA:SA-1:1, 16.3 mM acetic acid [Example 1] and LWGA:SA-1:0.4, 8.2 mM acetic acid [Example 2]) were selected, and whether coacervate protects EGF from protease was evaluated. After incubation with 417 μg/ml trypsin-EDTA at 37° C. and 100 rpm for 1 to 2 hr, EGF was mostly digested in free EGF and EGF-mixture. However, EGF in EGF-coacervate was protected for a maximum of 2 hr (FIG. 7).

5. In-vitro release from EGF-coacervate

Figure 8:
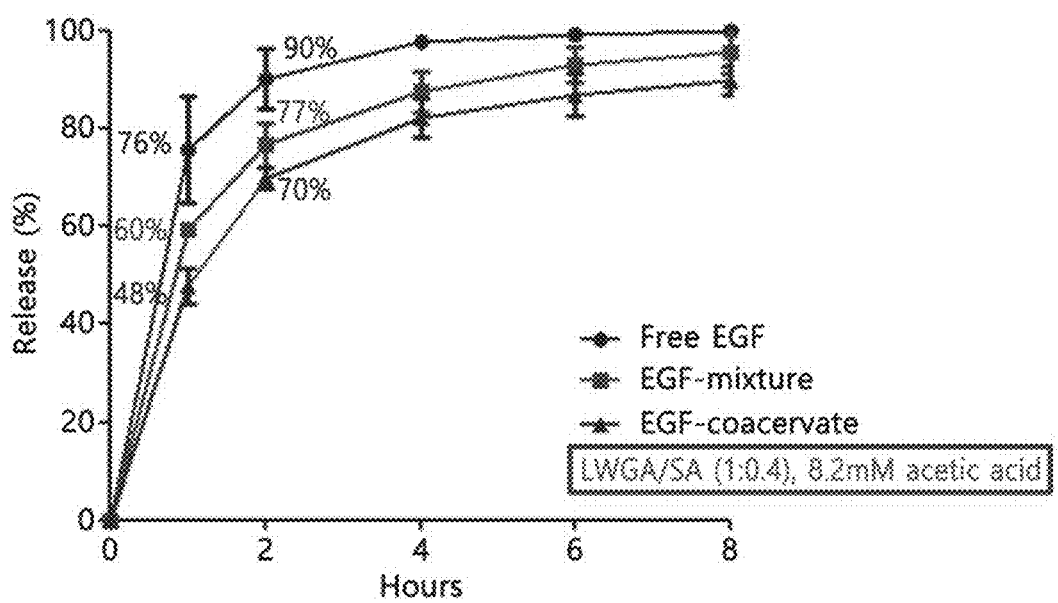
FIG. 8 shows an in-vitro release pattern graph using a Transwell (32° C., 150 rpm), in which a release test of EGF from free EGF, EGF-mixture and EGF-coacervate (LWGA:SA-1:0.4 ratio) was performed and measured through HPLC.
Figure 12:
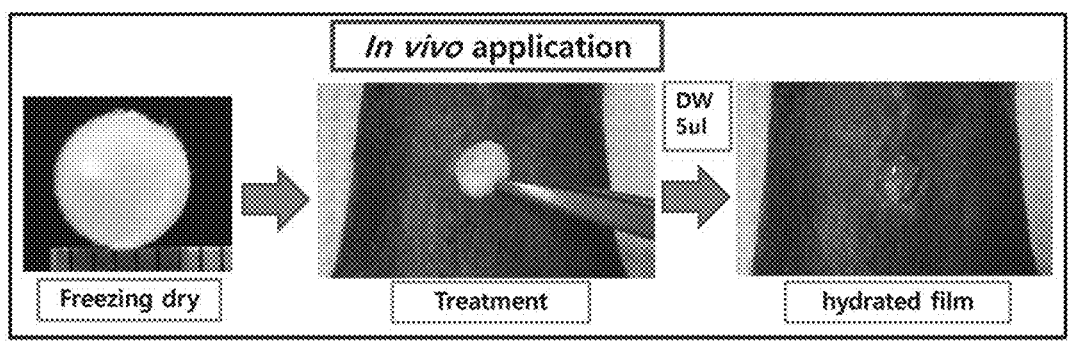
FIG. 12 is images showing the application of lyophilized EGF-coacervate or EGF mixture to in-vivo testing.

EGF-coacervate and EGF-mixture were lyophilized in order to facilitate local delivery in a sustained manner during wound healing. When the lyophilized sample is in contact with a Transwell, it is instantly hydrated to form a film (FIG. 12). As shown in FIG. 8, EGF-coacervate showed slow release from lyophilized EGF-coacervate compared to lyophilized EGF-mixture and free EGF solution.

6. Promotion of cell bioactivity of optimized EGF-coacervate

A. Analysis of cell proliferation

Figure 9:
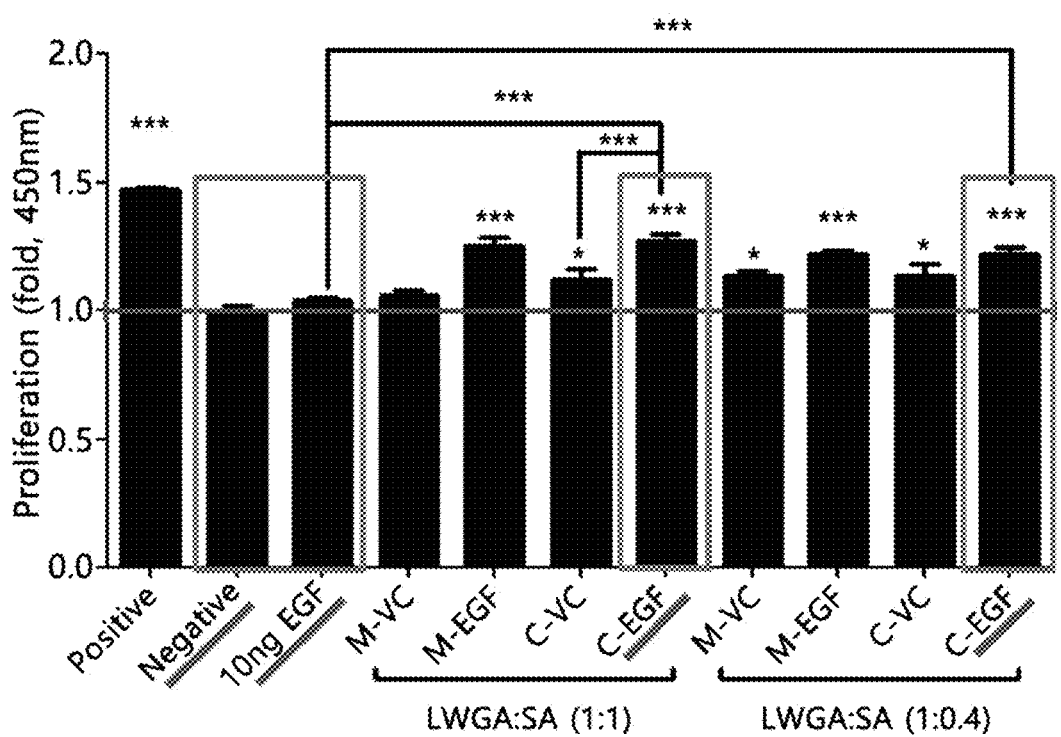
FIG. 9 is a graph showing the effect of EGF-coacervate on the proliferation of HDF.

The effects of free EGF, formulation control (the formulation composition is the same but the drug is not included), EGF-mixture and EGF-coacervate on cell proliferation capacity of FIDF cell proliferation capacity of HDF under two different conditions of coacervate were measured through cell counting kit-8 analysis, 10 ng/ml of free EGF had no significant effect on the proliferation of HDF compared to the negative control. However, EGF-mixture and EGF-coacervate significantly increased the proliferation activity of HDF compared to the negative control and free EGF (FIG. 9).

B. Analysis of cell migration

Figure 10:
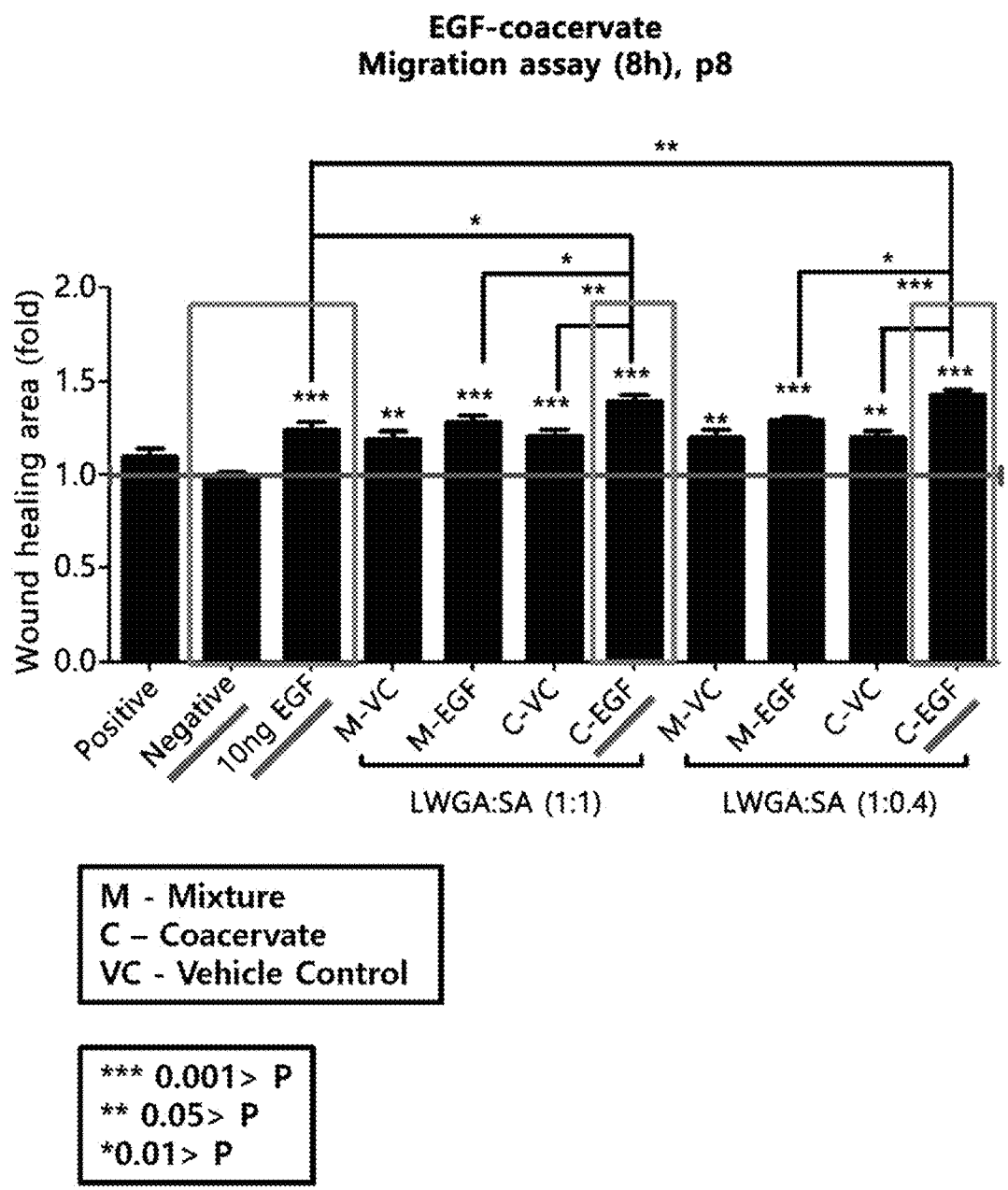
FIG. 10 shows the results of quantitative analysis of the effect of EGF-coacervate on the migration of HDF (M: mixture, C: coacervate, VC: vehicle control)
Figure 11:
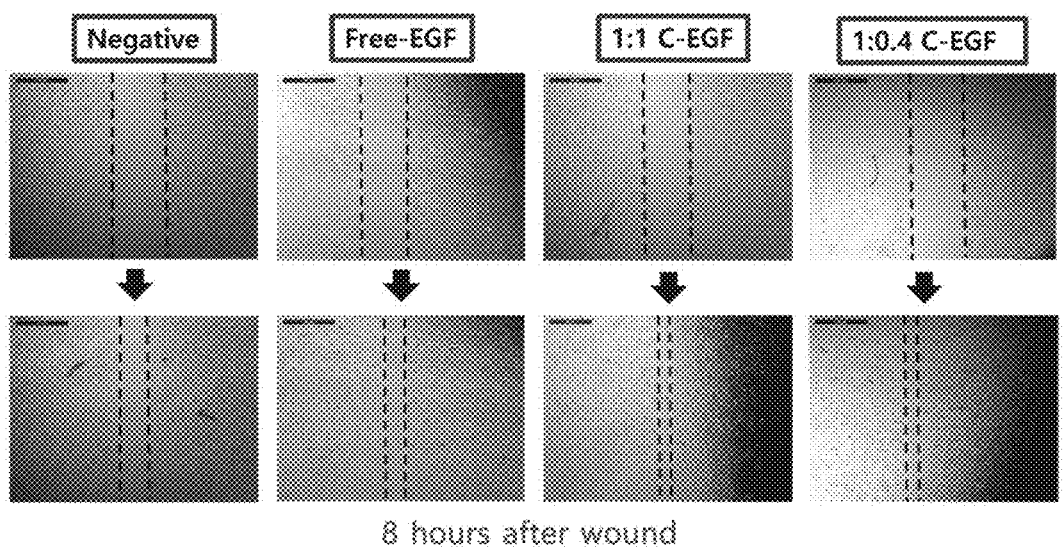
FIG. 11 is images showing the effect of EGF-coacervate on the migration of HDF, in which, after incubation for 8 hrs. in a medium containing 10 ng/ml of free EGF and lyophilized samples (vehicle control, EGF-mixture, EGF-coacervate), images of scratches in the confluent HDFs monolayer are illustrated (scale bar=500 µm)

The effects of free EGF, formulation control (the formulation composition is the same but the drug is not included), EGF-mixture, and EGF-coacervate (coacervate under two different conditions) on cell migration capacity of HDF were measured through the activity of inducing in-vitro wound closure in the scratch assay. 10 ng/ml of free EGF showed a significant migration effect in HDF compared to the negative control. At the same concentration, EGF-coacervate significantly increased the migration activity of HDF compared to the negative control, free EGF and EGF-mixture (FIGS. 10 and 11).

7. Promotion of wound healing of optimized EGF-coacervate

Figure 13:
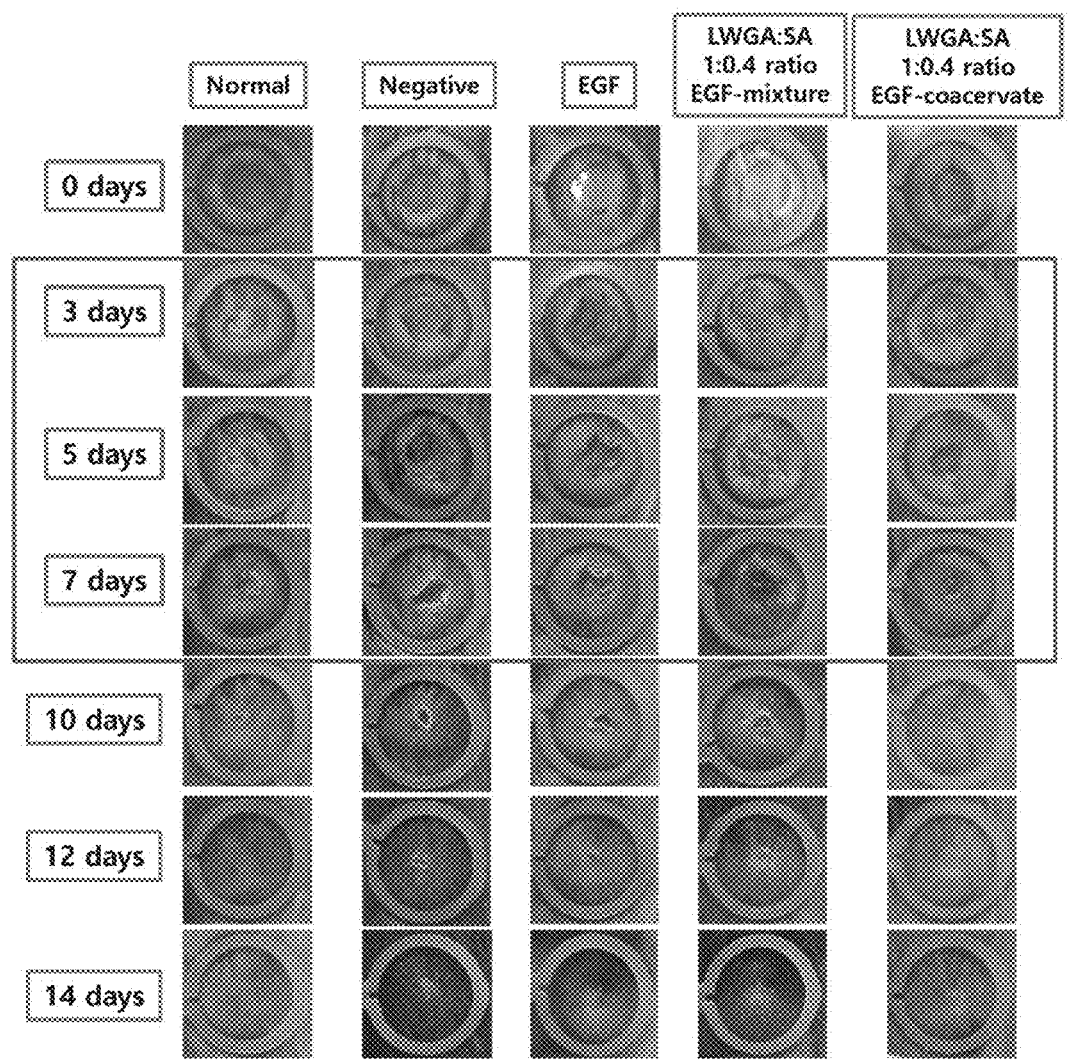
FIG. 13 shows the effect of EGF-coacervate on wounds during in-vivo testing using an STZ-induced diabetic mouse model, in which wounds are treated with DPBS (normal, negative control), free EGF, EGF-mixture, and EGF-coacervate.
Figure 14:
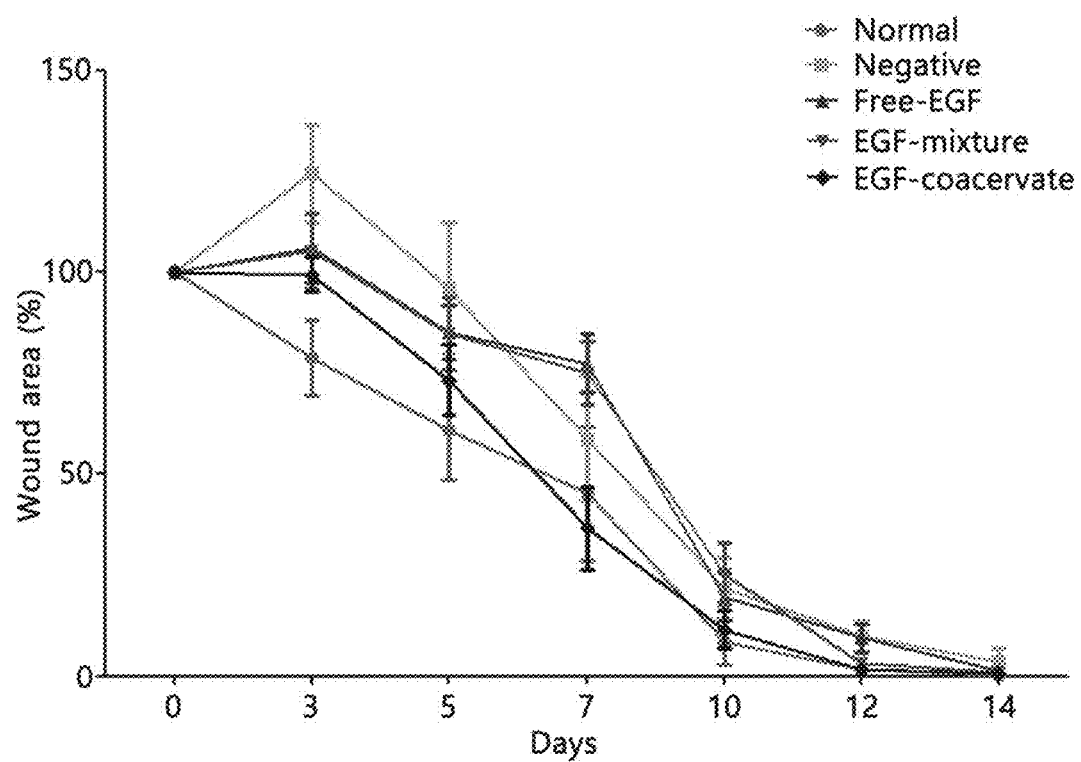
FIG. 14 is a graph showing the effect of EGF-coacervate on wounds during in-vivo testing using an STZ-induced diabetic mouse model, in which the extent of closure of wounds treated with DPBS (normal, negative control), free EGF, EGF-mixture, and EGF-coacervate over time is represented as the percentage relative to the original wound area.

The effect of free EGF, EU-mixture and EGF-coacervate on wound closure was evaluated in wounds using a diabetes-induced mouse model. Among two conditions selected for efficacy testing, LWGA:SA-1:0.4, 8.2 mM acetic acid EGF-coacervate (referred to as 'optimized EGF-coacervate') exhibited high encapsulation efficiency compared to the LWGA:SA-1:1, 16.3 mM acetic acid EGF-coacervate, and was used for in-vivo testing. Wounds were administered with DPBS in the normal and negative control groups. 1 μg/10 μl of free EGF was administered in the free-EGF group and 1 μg of EGF/lyophilized material was administered in the EGF-mixture and EGF-coacervate groups. The lyophilized EU-mixture and EGF-coacervate were applied to the wound and wetted with 5 μl of DW (FIG. 12). The sample was treated two times on day 0 and day 3 after injury. The wound site was observed for 14 days (n=5). The closure of the wound treated with the EGF-coacervate was effectively accelerated compared to the negative control, free EGF, and EGF-mixture throughout the test period. After 7 days, the wound of EGF-coacervate was almost the same as the normal group, rather than the diabetes-induced group. The normal and EGF-coacervate groups accelerated wound closure within 12 days (FIGS. 13 and 14).

In the present disclosure, whether the EGF-coacervate system using a natural polymer improves the wound-healing process by protecting EGF from proteolysis due to increased protease in chronic wounds was observed. Thereby, the coacervation composition and reaction conditions of the EGF-coacervate delivery system including gelatin A and sodium alginate were successfully obtained. EGF encapsulated in optimized EGF-coacervate was protected from trypsin digestion. EGF delivered by the coacervate-based system exhibited superior activity compared to free EGF not only in in-vitro HDF proliferation and migration testing but also in in-vivo diabetic mouse wound models. Based on these results, EGF-coacervate is proposed as a potential EGF delivery system that accelerates the wound-healing process of chronic wounds such as DFU.

What is claimed is:

1. A coacervate composition for use in a wound-healing agent for healing a wound, the coacervate composition comprising a protein drug, gelatin A, sodium alginate and an acid, wherein a weight ratio of the gelatin A:the sodium alginate is 1:1 to 1:1.2, wherein the acid is 8.2 mM to 16.3 mM acetic acid, wherein pH is 4.14 to 4.38, and wherein the gelatin A has an average molecular weight of 20 KDa to 25 KDa.

2. The coacervate composition of claim 1, wherein the weight ratio of the gelatin A:the sodium alginate is 1:1.

3. The coacervate composition of claim 1, wherein the protein drug is at least one selected from the group consisting of epidermal growth factor (EGF), growth hormone (GH) and fibroblast growth factor (FGF).

4. A wound-healing agent for healing a wound, the wound-healing agent comprising the coacervate composition of claim 1.

5. The wound-healing agent of claim 4, wherein the wound is a chronic intractable wound.

6. The wound-healing agent of claim 4, wherein the wound is a diabetic ulcer.

7. The wound-healing agent of claim 4, wherein the wound is a diabetic foot ulcer.

8. The wound-healing agent of claim 4, wherein the weight ratio of the gelatin A:the sodium alginate is 1:1.

9. The coacervate composition of claim 1, wherein the protein drug is contained in an amount of 100 ng/g to 100 μg/g, and the sodium alginate is contained in an amount of 1 mg/g to 2.5 mg/g.

10. A method of making a wound-healing agent for healing a wound, the method comprising:
providing the coacervate composition of claim 1; and
lyophilizing the coacervate composition to obtain the wound-healing agent.

11. A coacervate composition for use in a wound-healing agent for healing a wound, the coacervate composition comprising a protein drug, gelatin A, sodium alginate and an acid, wherein a weight ratio of the gelatin A:the sodium alginate is 1:0.8, wherein the acid is 8.2 mM to 10.9 mM acetic acid, or 16.3 mM acetic acid, wherein pH is 4.27 to 4.39, or is equal to or greater than 4.12 and less than 4.20, and wherein the gelatin A has an average molecular weight of 20 KDa to 25 KDa.

12. The coacervate composition of claim 11, wherein the weight ratio of the gelatin A:the sodium alginate is 1:0.8 and wherein the acid is 8.2 mM to 10.9 mM acetic acid.

13. A method of making a wound-healing agent for healing a wound, the method comprising:

providing the coacervate composition of claim 11; and
lyophilizing the coacervate composition to obtain the wound-healing agent.

14. A coacervate composition for use in a wound-healing agent for healing a wound, the coacervate composition comprising a protein drug, gelatin A, sodium alginate and an acid, wherein a weight ratio of the gelatin A:the sodium alginate is 1:0.4, wherein the acid is 5.4 mM to 8.2 mM acetic acid, wherein pH is 4.34 to 4.52, and wherein the gelatin A has an average molecular weight of 20 KDa to 25 KDa.

15. A method of making a wound-healing agent for healing a wound, the method comprising:
providing the coacervate composition of claim 14; and
lyophilizing the coacervate composition to obtain the wound-healing agent.

\* \* \* \* \*